(12) United States Patent
Schacht

(10) Patent No.: US 11,465,825 B2
(45) Date of Patent: Oct. 11, 2022

(54) SYSTEMS AND METHODS FOR DISPENSING STERILE ITEMS

(71) Applicant: Stefan Richard Schacht, Bellingham, WA (US)

(72) Inventor: Stefan Richard Schacht, Bellingham, WA (US)

(*) Notice: Subject to any disclaimer, the term of this patent is extended or adjusted under 35 U.S.C. 154(b) by 175 days.

(21) Appl. No.: 16/893,163

(22) Filed: Jun. 4, 2020

(65) Prior Publication Data

US 2020/0385199 A1 Dec. 10, 2020

Related U.S. Application Data

(60) Provisional application No. 62/857,160, filed on Jun. 4, 2019.

(51) Int. Cl.

| | |
|---|---|
| *A47K 10/36* | (2006.01) |
| *B65D 83/08* | (2006.01) |
| *A61F 15/00* | (2006.01) |
| *A61B 42/40* | (2016.01) |
| *A61M 5/00* | (2006.01) |

(52) U.S. Cl.
CPC .......... *B65D 83/0811* (2013.01); *A47K 10/36* (2013.01); *A61B 42/40* (2016.02); *A61F 15/002* (2013.01); *A61M 5/002* (2013.01)

(58) Field of Classification Search
CPC .................................................. B65D 83/0811
See application file for complete search history.

(56) References Cited

U.S. PATENT DOCUMENTS

| | | | | |
|---|---|---|---|---|
| 8,322,262 | B2* | 12/2012 | Ryu ..................... | B65H 37/005 83/649 |
| 2007/0191753 | A1* | 8/2007 | Wendorf ............... | A61F 15/001 602/58 |
| 2015/0374441 | A1* | 12/2015 | Machado ............... | A61B 42/40 221/2 |

FOREIGN PATENT DOCUMENTS

WO     2013010144 A3     4/2013

* cited by examiner

*Primary Examiner* — Gene O Crawford
*Assistant Examiner* — Ayodeji T Ojofeitimi
(74) *Attorney, Agent, or Firm* — Schacht Law Office, Inc.; Michael R. Schacht

(57) ABSTRACT

A dispensing system for items comprises a main housing and a cartridge assembly. The cartridge assembly comprises a carrier reel, distal and proximal take-up reels, and a packaging strip comprising first and second strip portions detachably secured to define a plurality of item chambers, where at least one item is enclosed within each of the item chambers. The main housing assembly defines a dispensing opening and comprises a drive system. The drive system is operatively connected to the proximal and distal take-up reels. Operation of the drive system rotates the distal and proximal take-up reels such that operation of the drive system rotates the distal and proximal take-up reels such that the packaging strip is unwound from the main wheel, the first strip portion is wound onto the distal take-up reel, the second strip portion is wound onto the proximal take-up reel, and the items are dispensed through the dispensing opening.

16 Claims, 21 Drawing Sheets

SYSTEMS AND METHODS FOR DISPENSING STERILE ITEMS

RELATED APPLICATIONS

This application, U.S. patent application Ser. No. 16/893,163 filed Jun. 4, 2020, claims benefit of U.S. Provisional Application Ser. No. 62/857,160 filed Jun. 4, 2019, the contents of which are incorporated herein by reference.

TECHNICAL FIELD

The present invention relates to dispensing systems and methods and, more particular, to systems and methods for dispensing sterile items.

SUMMARY

The present invention may be embodied as a dispensing system for items comprising a main housing assembly and a cartridge assembly. The main housing assembly defines a dispensing opening and comprises a drive system. The cartridge assembly comprises a carrier reel, distal and proximal take-up reels, and a packaging strip comprising first and second strip portions detachably secured to define a plurality of item chambers, where at least one item is enclosed within each of the item chambers. The carrier reel is adapted to store the packaging strip. The distal take-up reel is operatively connected to the first strip portion. The proximal take-up reel is operatively connected to the second strip portion. The drive system is operatively connected to the proximal and distal take-up reels. Operation of the drive system rotates the distal and proximal take-up reels such that operation of the drive system rotates the distal and proximal take-up reels such that the packaging strip is unwound from the main wheel, the first strip portion is wound onto the distal take-up reel, the second strip portion is wound onto the proximal take-up reel, and the items are dispensed through the dispensing opening.

The present invention may also be embodied as a method of dispensing items comprising the following steps. First and second packaging strip portions are provided. A packaging strip is formed by adhering the first packaging strip portion to the second packaging strip portion such that each of the items is sealed within an item chamber. At least a portion of the packaging strip is arranged on a carrier reel. A first packaging strip portion end of the first packaging strip portion is secured to a distal take-up reel. A second packaging strip portion end of the second packaging strip portion is secured to a proximal take-up reel. The carrier reel, the packaging strip, and the distal and proximal take-up reels are supported on a cartridge plate. A cartridge assembly is formed by engaging the cartridge plate with a cartridge housing. A main housing defining a dispensing opening is provided. A drive system is supported on the main housing. The cartridge assembly is supported within the main housing such that the drive system engages the distal and proximal take-up reels. Items are dispensed through the dispensing opening by operating the drive system to rotate the distal and proximal take-up reels such that the packaging strip is unwound from the main wheel, the first strip portion is wound onto the distal take-up reel, and the second strip portion is wound onto the proximal take-up reel.

The present invention may also be embodied as a dispensing system for items comprising a main housing assembly and a cartridge assembly. The main housing assembly defines a dispensing opening and comprising a drive system. The cartridge assembly comprises a cartridge plate, a cartridge housing that engages the cartridge plate to define a cartridge chamber, a carrier reel supported by the cartridge plate within the cartridge chamber, distal and proximal take-up reels supported by the cartridge plate within the cartridge chamber, and a packaging strip comprising first and second strip portions detachably secured to define a plurality of item chambers, where at least one item is enclosed within each of the item chambers. The carrier reel is adapted to store the packaging strip. The distal take-up reel is operatively connected to the first strip portion. The proximal take-up reel is operatively connected to the second strip portion. The drive system is operatively connected to the proximal and distal take-up reels such that operation of the drive system rotates the distal and proximal take-up reels such that the packaging strip is unwound from the main wheel, the first strip portion is wound onto the distal take-up reel, the second strip portion is wound onto the proximal take-up reel, and the items are dispensed through the dispensing opening.

DETAILED DESCRIPTION

Figure 1:
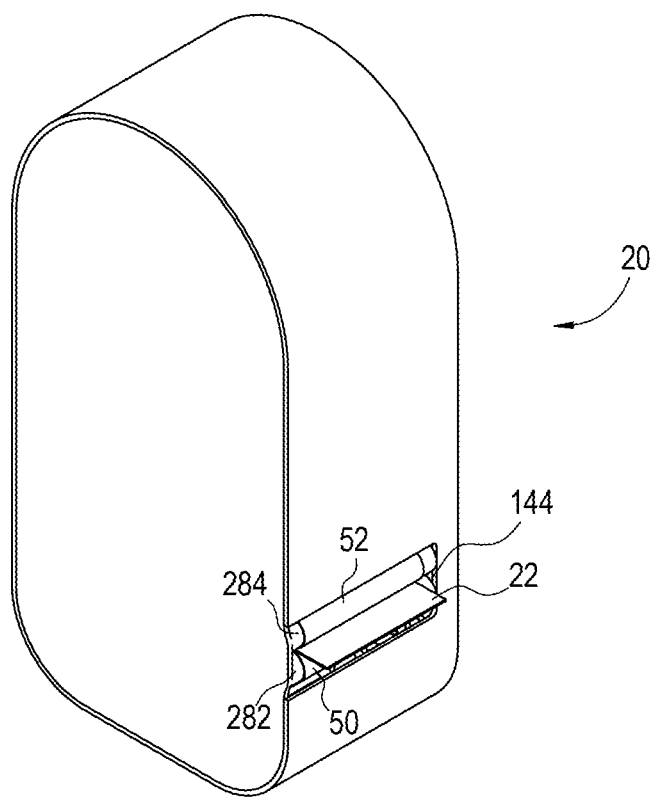
FIG. 1 is an isometric view of a first example dispensing system of the present invention.
Figure 2:
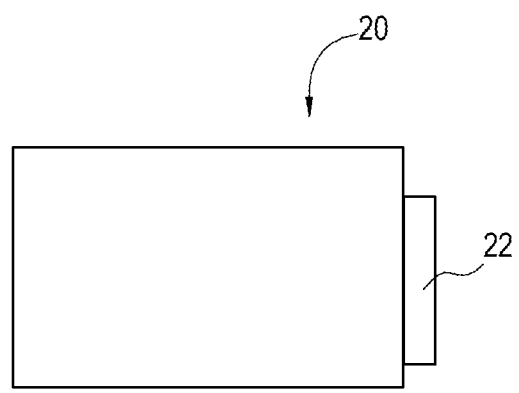
FIG. 2 is a top plan view of the first example dispensing system.

Referring initially to FIG. 1 of the drawing, depicted therein is a first example dispensing system 20 constructed in accordance with, and embodying, the principles of the present invention. The first example dispensing system 20 is configured to dispense items 22.

Figure 5:
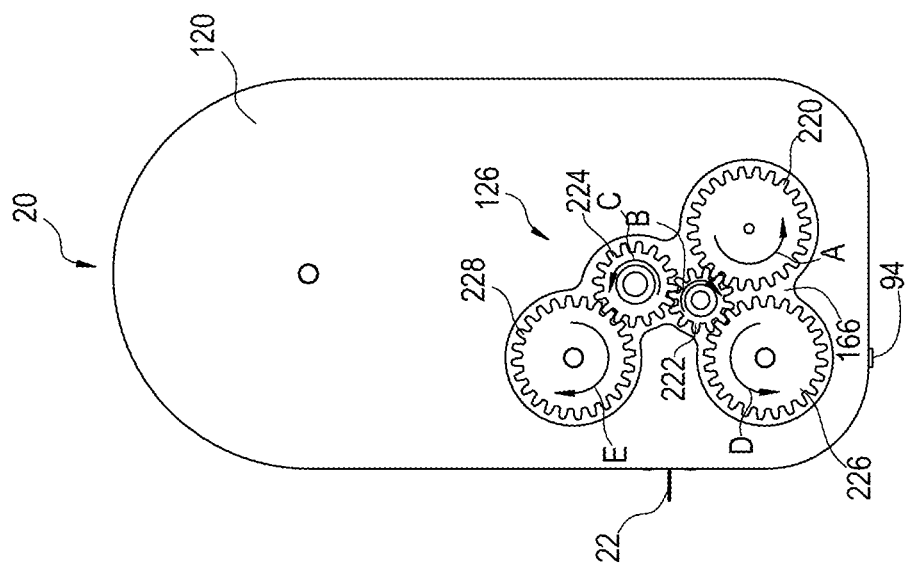
FIG. 5 is a second side elevation view of the first example dispensing system with a drive cover removed.
Figure 4:
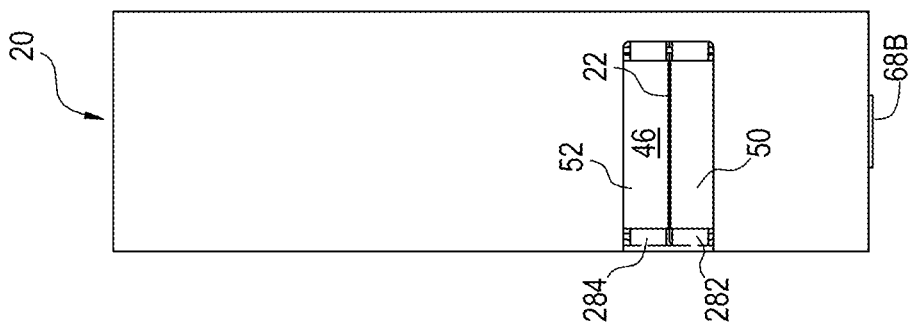
FIG. 4 is a front elevation view of the first example dispensing system.
Figure 3:
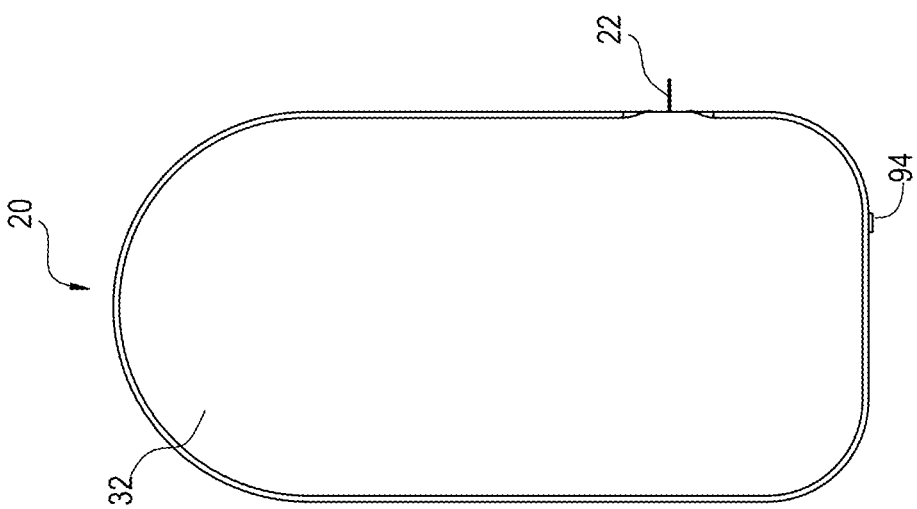
FIG. 3 is a first side elevation view of the first example dispensing system.

The first example dispensing system 20 comprises a main housing assembly 30 (FIG. 7), a cartridge assembly 32 (FIGS. 9 and 10), a drive assembly 34 (FIGS. 5 and 11), and a control system 36 (FIGS. 12, 14, 21, and 22). The example main housing assembly 30 is configured to be supported at a predetermined location such as a wall or podium. The example cartridge assembly 32 is configured to contain a plurality of the items 22 and is adapted to be detachably supported by the main housing assembly 30. The example drive system 34 is adapted to be supported at least in part by the main housing assembly 32 and may be supported in part by the cartridge assembly 32. The example drive system 34 causes movement that automatically dispenses the items 22. The example control system 36 is supported by the at least one of the main housing assembly 30 and the cartridge assembly 32 to control operation of the drive system 34.

With the example cartridge assembly 32 supported by the main housing assembly 30, a user interacts with the control system 36 in a predetermined manner. When the user interacts with the control system 36 in the predetermined manner, the control system 36 controls the drive system 34 to operate such that an item 22 at least partly extends from the dispensing system 20 as shown in FIG. 1. The user grasps and pulls on the item 22 to remove the item from the dispensing system 20. Each item 22 is dispensed without exposing the next item 22 to be dispensed to contamination.

With the foregoing general understanding of the construction and operation of the first example dispensing system 20 in mind, the details of the first example dispensing system 20 will now be described in further detail.

The first example dispensing system 20 is configured to minimize contamination when sterile items are dispensed to multiple successive users. The items 22 to be dispensed are thus typically, but not necessarily, sterile items or products.

Figure 13:
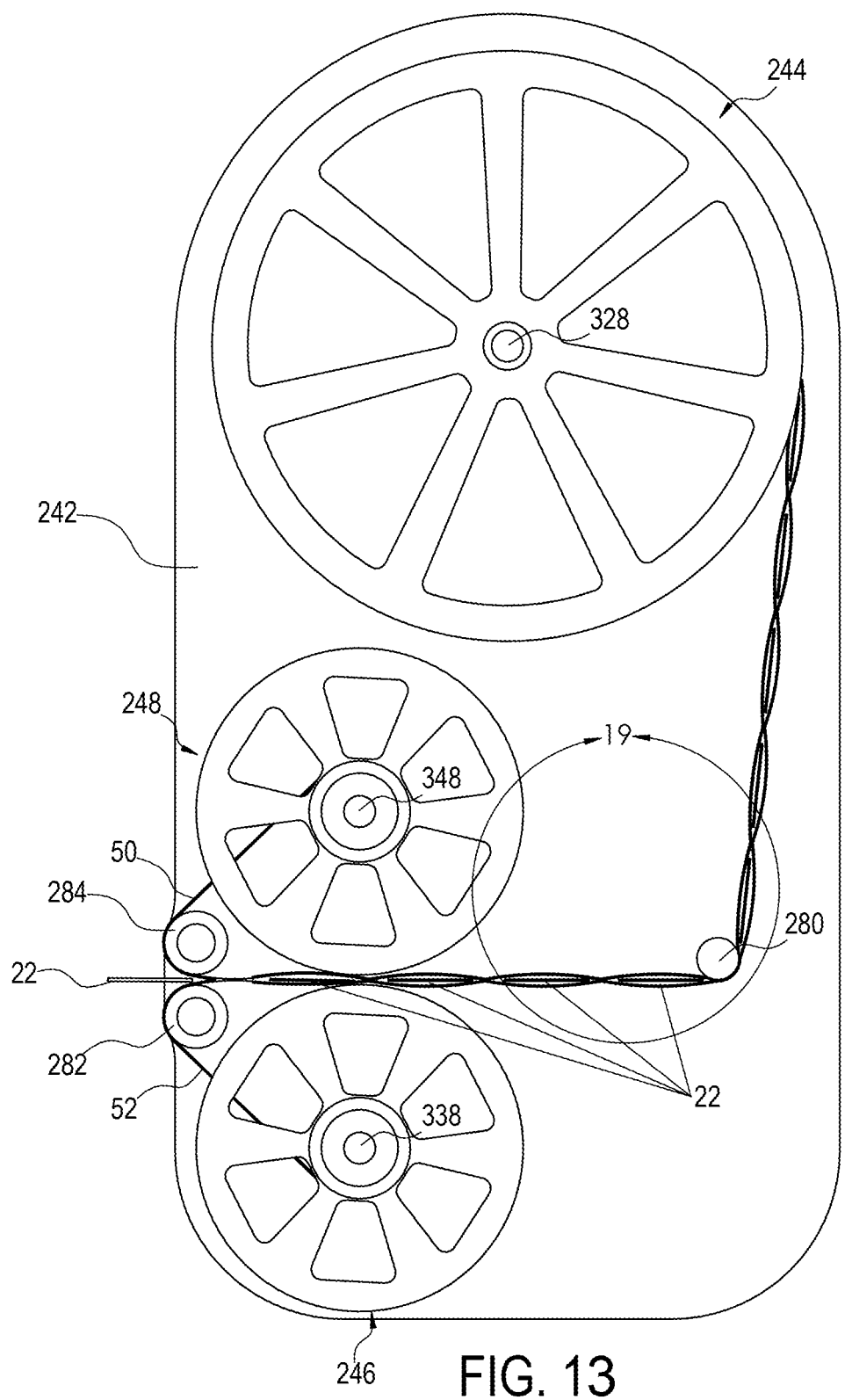
FIG. 13 is a side elevation view illustrating the cartridge plate, carrier reel, and first and second take-up reels and also depicting a packaging strip of items being dispensed.

As perhaps best shown in FIG. 13, the items 22 to be dispensed are typically items that can be enclosed in item chambers 40 that form a part of a packaging strip 42 containing a plurality of such item chambers 40. The items 22 thus exist in a sterile environment when contained inside the package strip 42.

The width and length dimensions of the item chambers 40 are determined by the size, dimensions, and characteristics (e.g., relative rigidity) of the particular item 22 to be dispensed. The width dimensions of the item chambers 40 will in turn determine the width dimensions of the packaging strip 42. The number of item chambers and the length dimensions of the item chambers 40 included in each packaging strip 42 will determine the length dimension of the entire packaging strip 42. The characteristics of the items 22 and the width and length dimensions of the packaging strip 42 will determine the size and dimensions of a roll of the packaging strip 42 containing the items 22 and thus of the first example dispensing system 20. The first example dispensing system 20 may be scaled up or down to accommodate the characteristics of the items 22 and the dimensions of the item chambers 40 and the packaging strip 42 containing the items 22 to be dispensed.

The items 22 may be flexible, such as bandages, face masks, gloves, or the like, or at least partly rigid, such as cotton swabs, syringes, needles, or the like. If the items 22 are flexible, the longitudinal item axis of the items 22 may be arranged perpendicular, parallel, or angled with respect to a longitudinal strip axis of the packaging strip 42. If the times 22 are at least partly rigid, however, the items 22 may be arranged such that the longitudinal item axis of the items 22 is angled or perpendicular with respect to the longitudinal strip axis of the packaging strip 42 to facilitate rolling of the packaging strip 42 as will be described in further detail below.

Each item chamber 40 may contain more than one item. For example, an item chamber 40 may contain a syringe and a prep pad for sterilizing an area prior to an injection. As another example, an item chamber 40 may contain face coverings such as surgical masks and hand coverings such as examination gloves.

Further, the first example dispensing system 20 may be configured to dispense multiple types of items, with item chambers for each item type being of different sizes. For example, one item chamber 40 may contain a syringe and the next item chamber 40 may contain a prep pad. In this first example, the syringes when stored may be bigger than prep pads when stored, in which case the item chambers 40 containing the syringes may be bigger than the item chambers 40 containing prep pads. As a second example, the item chambers 40 may alternate between containing face coverings such as surgical masks and hand coverings such as examination gloves. In the second example, the face coverings when stored may be bigger than gloves when stored, in which case the item chambers 40 containing the face coverings may be bigger than the item chambers 40 containing gloves.

The first example dispensing system 20 is configured to dispense items 22 in the form of bandages of the same size, and that application of the present invention will be described in reference to the first example dispensing system 20. The example items 22 will thus alternatively be described herein as bandages of the same size with the understanding that items other than bandages and of different sizes may form the dispensed items 22.

Figure 19:
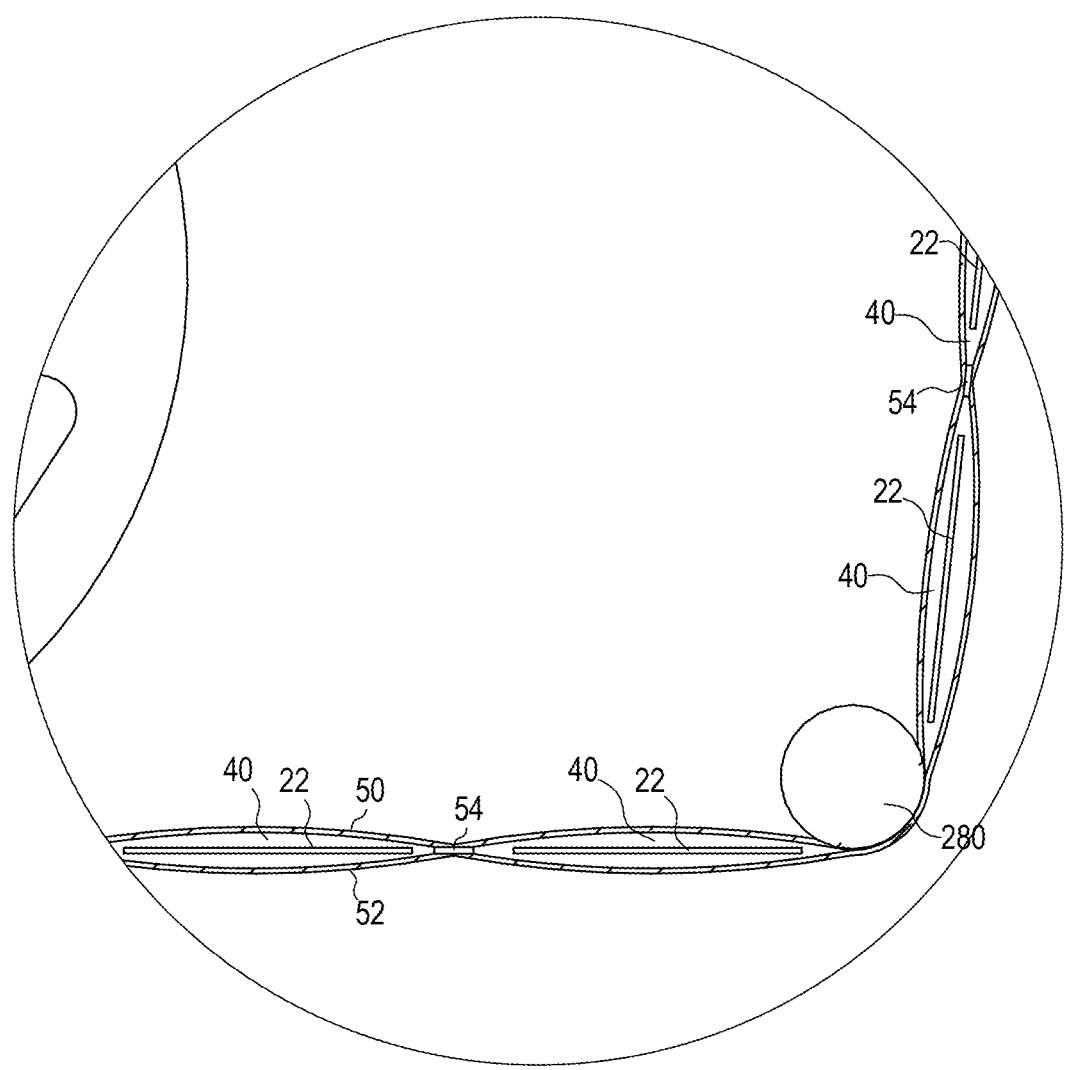
FIG. 19 is a detail of FIG. 14.
Figure 21:
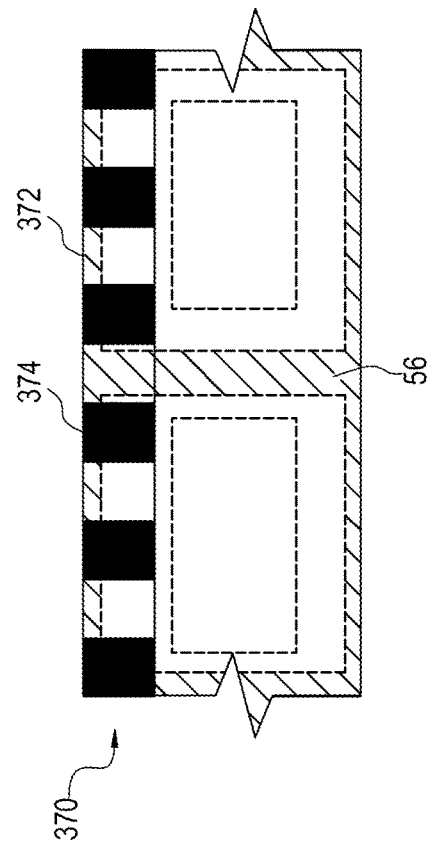
FIG. 21 is a plan view of a section of a first example packaging strip carrying items to be dispensed.

Referring again to FIGS. 13 and 14 of the drawing, it can be seen that the example packaging strip 42 comprises first and second strip portions 50 and 52. The strip portions 50 and 52 are detachably attached to define the item chambers 40. The example strip portions 50 and 52 are impermeable to contamination and are detachably attached by an adhesive layer 54 as shown FIG. 19. As shown in FIG. 21, the adhesive layer 54 is within an adhesive region 56 (illustrated by cross-hatching in FIG. 21) such that the adhesive layer 54 and the material forming the strip portions 50 and 52 forms a seal around each of the item chambers 40 to prevent inhibit contamination of the items 22 during normal use.

The strip portions 50 and 52 and adhesive layer 54 are capable of sealing the item chambers 40 during normal handling and use of the packaging strip 42 prior to dispensing of any particular item 22. However, the adhesive 54 is formulated such that the application of a peeling force to the strip portions 50 and 52 allows the strip portions 50 and 52 to be peeled away from each other to overcome the adhesion of the adhesive 54 without tearing the strip portions 50 and 52. The structure of the strip portions 50 and 52, the formulation of the adhesive 54, and the formation of the packaging strip 42 by applying the adhesive 54 in the adhesive region 56 and bringing the strip portions 50 and 52 together are or may be conventional and will not be described herein in detail.

Figure 7:
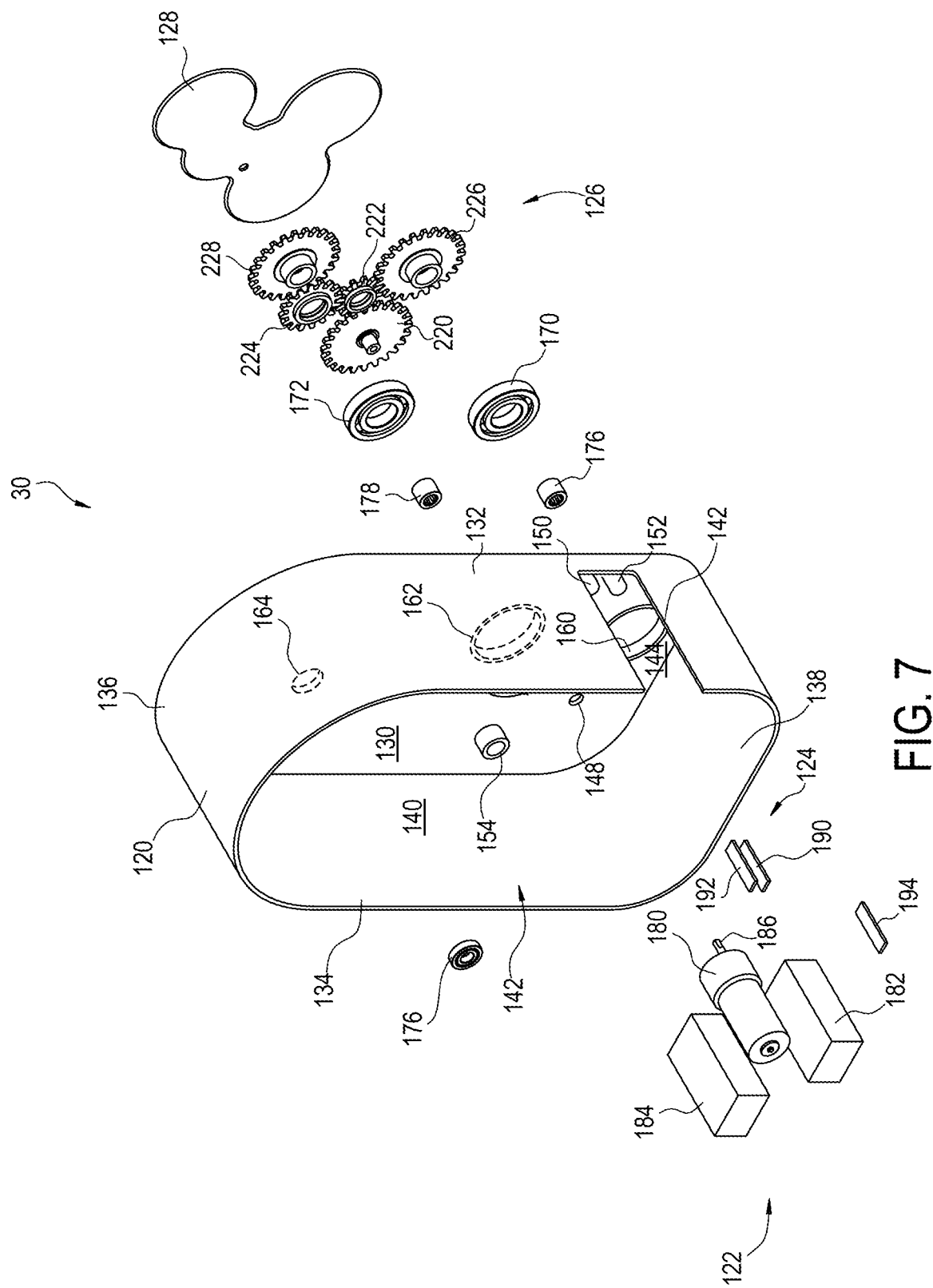
FIG. 7 is an exploded view of the first example main housing assembly.

Turning now to FIG. 7, the example main housing assembly 30 will now be described in further detail. The example main housing assembly 30 comprises a main housing 120, a drive motor system 122, a sensor system 124, a transmission system 126, and a transmission cover 128. The example main housing 120 defines first main housing wall 130, a second main housing wall 132, a third main housing wall 134, a top main housing wall 136, and a bottom main housing wall 138. A main chamber 140 is defined by the main housing 120. Contiguous edges of the example second, third, top, and bottom main housing walls 132, 134, 136, and 138 define a main opening 142, and a dispensing slot 144 and a sensor opening 146 are formed in the example second wall 132. A drive opening 148 is formed in the first wall 130. The main chamber 140 may be accessed through the main opening 142 and/or the dispensing slot 144. The first example dispensing system 20 may be supported on a vertical surface (not shown) such as a wall or cabinet by fasteners (not shown) extending through openings (not shown) in the first main housing wall 130 or third main housing wall 134 or on a horizontal surface (not shown) by fasteners (not shown) extending through openings (not shown) in the top main housing wall 136 or bottom main housing wall 138.

Figure 15:
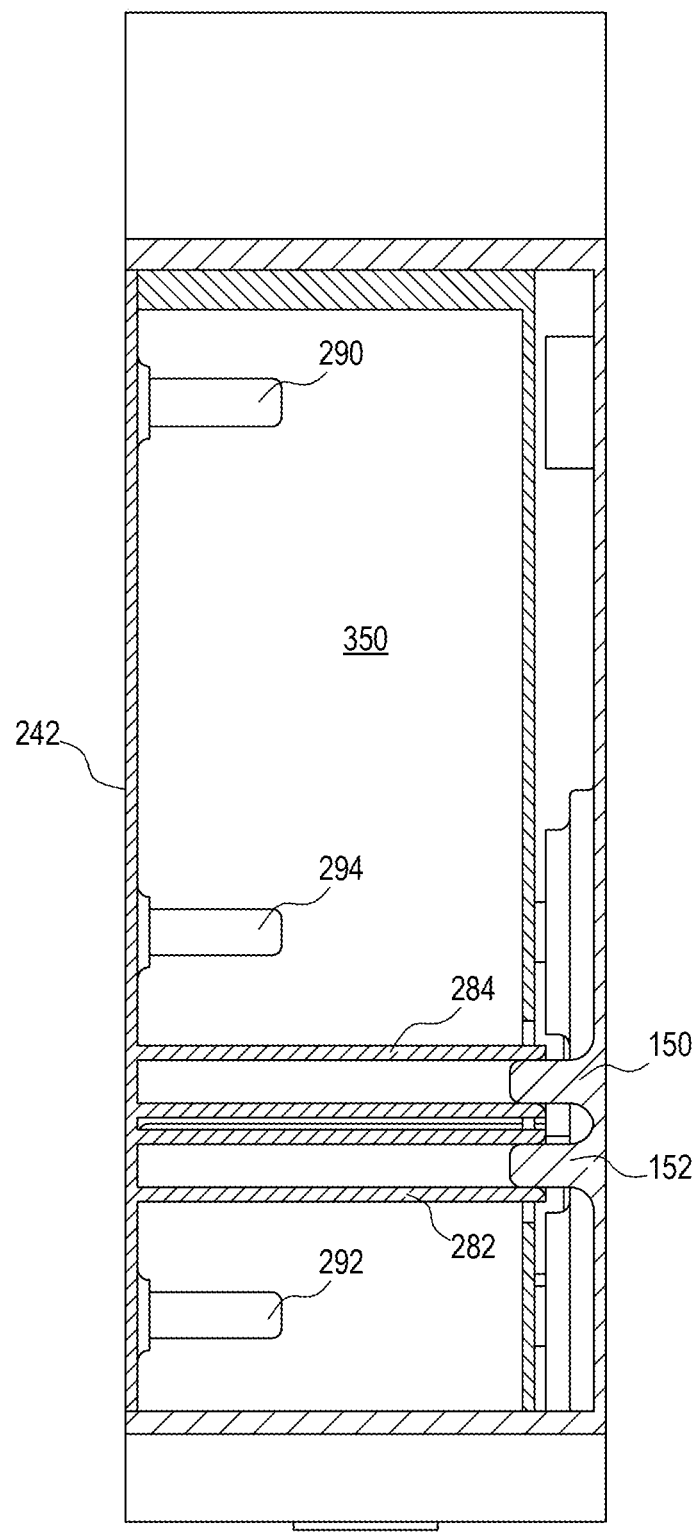
FIG. 15 is a section view taken along lines 15-15 in FIG. 14.
Figure 16:
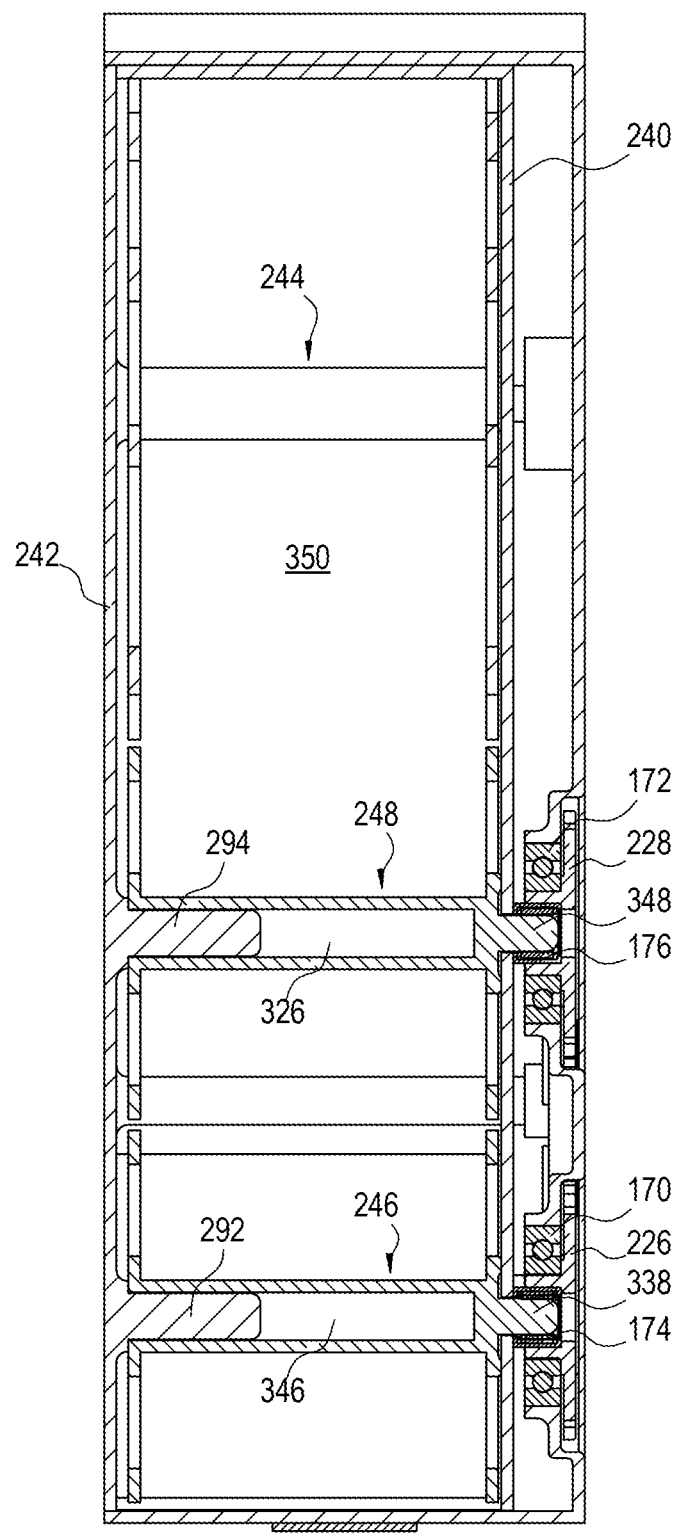
FIG. 16 is a section view taken along lines 16-16 in FIG. 14.
Figure 17:
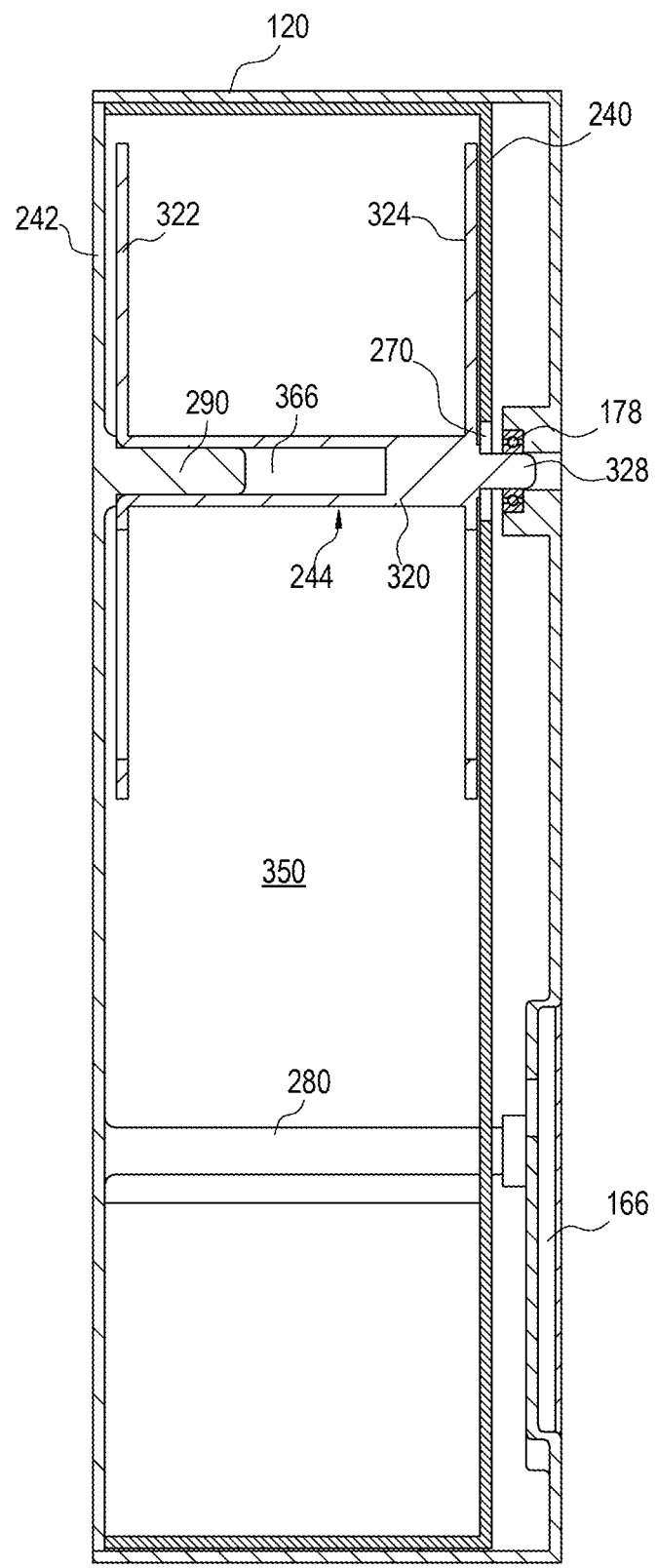
FIG. 17 is a section view taken along lines 17-17 in FIG. 14.
Figure 18:
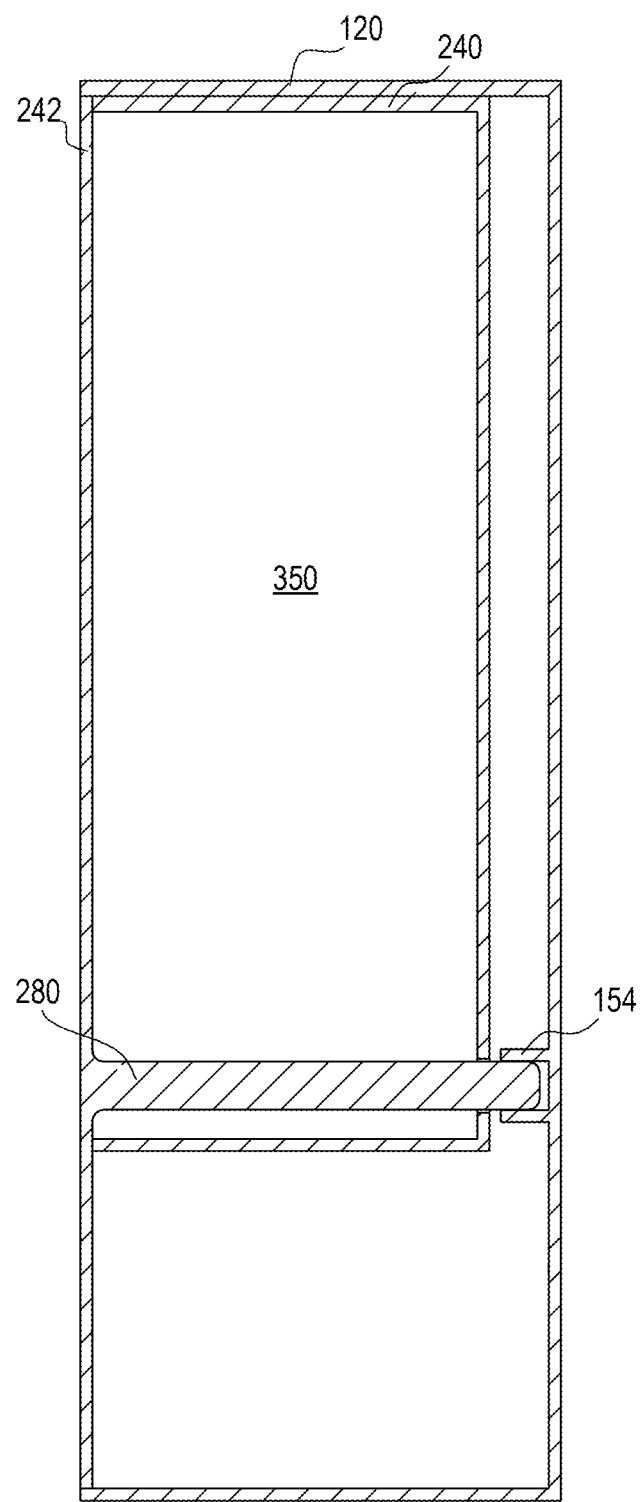
FIG. 18 is a section view taken along lines 18-18 in FIG. 14.

FIG. 7 illustrates that a main guide support 150 extends from the first main housing wall 130 into the main chamber 140. As best shown in FIGS. 14-18, formed in the first main housing wall 130 and extending into the main chamber 140 are first and second strip guide supports 152 and 154, first, second, and third bearing supports 160, 162, and 164 (FIGS. 16 and 17), a transmission support 166 (FIG. 17). First and second ring bearing assemblies 170 and 172 are supported by the example first and second bearing supports 160 and 162, respectively. A third ring bearing assembly 174 is supported by the third bearing support 164. The example transmission system 126 further comprises first and second inner bearing assemblies 176 and 178 support as will be described in further detail below. The example inner bearing assemblies 176 and 178 are unidirectional bearing assemblies. The example transmission system 124 is supported by the transmission support 166, and the transmission cover 128 is detachably attached to the main housing 120 to cover the transmission system 126 when supported by the transmission support 166.

Figure 6:
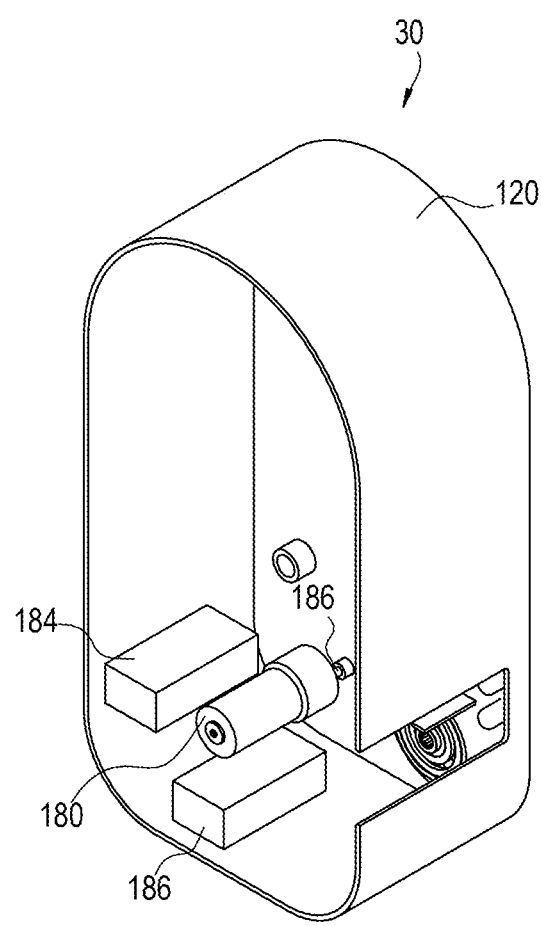
FIG. 6 is an isometric view of a first example main housing assembly of the first example dispensing system.

As perhaps best shown in FIGS. 6 and 7, the example drive motor system 122 comprises a drive motor 180, a power supply 182, and a controller 184. The drive motor 180 defines a drive shaft 186. The example sensor system 124 comprises an internal sensor 190, an optional light source 192, and an external sensor 194. The main housing 120 supports the drive motor 180 to engage the example transmission system 124 as will be described in further detail below. The main housing 120 further supports the power supply 182 and controller 184 in a location that does not interfere with mechanical operation of the first example dispensing system 20. The main housing 120 also supports the internal sensor 190 and light source 192 within the main chamber 140 and the external sensor 194 within the sensor opening 146 to allow the controller 184 to control the drive motor 180 based on input from the sensors 190 and 194 as will be described in further detail below.

The example drive motor 180 is an electric motor capable of rotating the drive shaft 186 based on a motor drive signal generated by the controller 184. The example power supply 182 comprises at least one of a converter for converting AC power to a voltage appropriate for operating the drive motor 180 and a battery for generating a voltage appropriate for operating the drive motor 180. The example controller 184 may be connected to a main server (not shown) through a WiFi, Bluetooth, and/or other wireless communications system. The controller 184 may transmit to the main server status information associated with the example dispensing system 20 such as number of items 22 remaining to be dispensed, battery level, and/or fault conditions. In particular, the controller 184 may send a low item notification data signal indicative of the need to replace an empty or near empty cartridge assembly 32 with a full cartridge assembly 32.

The internal sensor 190 is capable of reading strip data stored on the packaging strip 42. The data stored on the packaging strip 42 may be graphical data printed on the packaging strip, in which case the light source 192 may be used to illuminate the graphical data on the packaging strip 42. The data stored on the packaging strip 42 may take other forms such as magnetic, in which case the light source 192 may be omitted. The internal sensor 190 generates location data based on the strip data such that the controller 184 can generate the motor drive signal at least in part based on the location of the item chambers 40 relative to the dispensing slot 144.

The external sensor 194 is capable of interacting with a user of the first example dispensing system 20. One example of the external sensor 194 is a motion sensor that generates a dispense authorization signal based on movement (e.g., hand motion) indicative of the user's desire to dispense an item 22. Other examples of the external sensor 194 include any sensor or sensor system capable of generating a dispense authorization signal, including an optical sensor (e.g., motion or facial recognition software), a credit card reader for reading credit card information (e.g., chip or swipe), a near field communication (NFC) sensor capable of reading an identification card or fob, and/or a WiFi, Bluetooth, and/or other wireless communications system.

The example transmission system 126 comprises a primary drive gear 220, a secondary drive gear 222, a tertiary drive gear 224, and first and second take-up gears 226 and 228. The gears 220, 222, 224, 226, and 228 are supported by the transmission support 166 of the first main housing wall 130 as follows. The primary drive gear 220 is operatively connected to the drive shaft 186 through the drive opening 148 (FIG. 6) such that operation of the drive motor 180 causes rotation of the primary drive gear 220 as shown by Arrow A in FIG. 5. The primary drive gear 220 engages the secondary drive gear 222 such that rotation of the primary drive gear 220 causes rotation of the secondary drive gear 222 as shown by arrow B in FIG. 5. The secondary drive gear 222 engages the tertiary drive gear 224 and the first take-up gear 226 such that rotation of the secondary drive gear 222 causes rotation of the tertiary drive gear 224 as shown by arrow C in FIG. 5 and the first take-up gear 226 in a first take-up gear direction as shown by arrow D in FIG. 5. The tertiary drive gear 224 engages the second take-up gear 228 such that rotation of the tertiary drive gear 224 causes rotation of the second take-up gear 228 in a second take-up gear direction as shown by arrow E in FIG. 5, where the second take-up gear direction E is opposite the first take-up gear direction D. Operation of the drive motor 180 thus causes rotation of the first and second take-up gears 226 and 228 in opposite directions relative to the main housing 120. The example transmission system 126 is configured such that the first and second take-up gears 226 and 228 rotate at the substantially the same angular velocity.

The first and second ring bearing assemblies 170 and 172 support the first and second take-up gears 226 and 228 for free rotation relative to the main housing 120. The first and second inner bearing assemblies 174 and 176 are in turn supported by the first and second take-up gears 226 and 228, respectively, such that the first inner bearing assembly 176 is coaxially aligned with the first ring bearing assembly 170 and the second inner bearing assembly 178 is coaxially aligned with the second ring bearing assembly 172.

Referring now to FIGS. 8-18 of the drawing, the example cartridge assembly 32 will now be described in further detail. In FIGS. 9-12 and 15-18, the packaging strip 42 and items 22 contained packaged therein are not depicted for purposes of clarity and simplicity.

Figure 8:
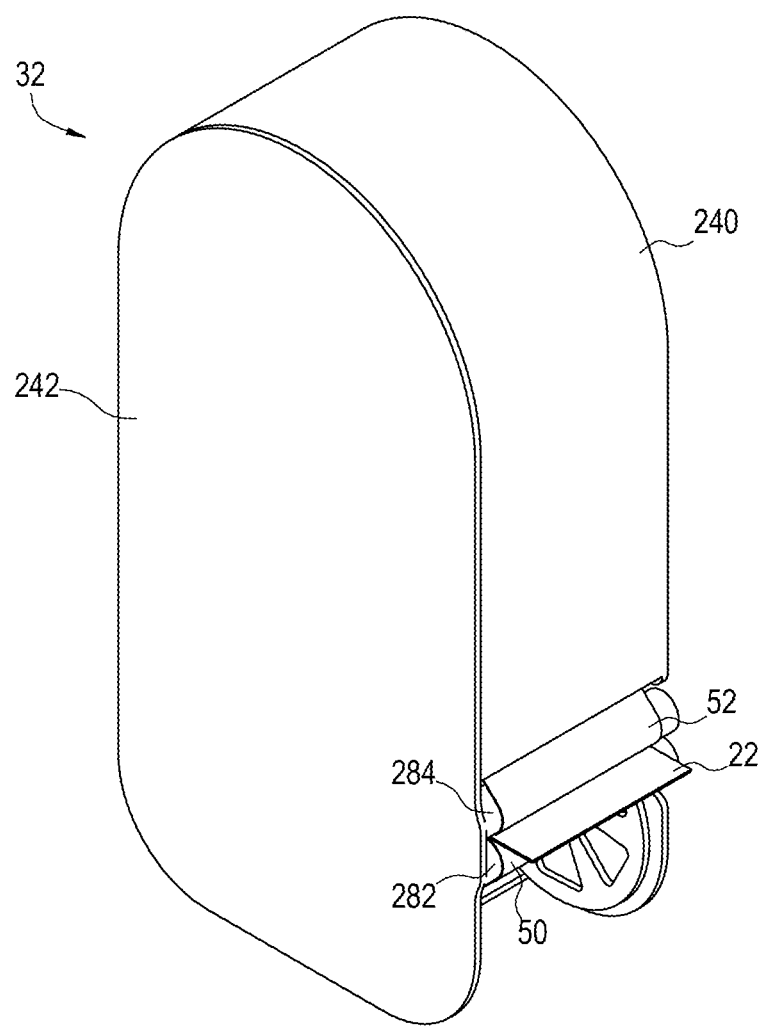
FIG. 8 is an isometric view of a first example cartridge assembly of the first example dispensing system.
Figure 9:
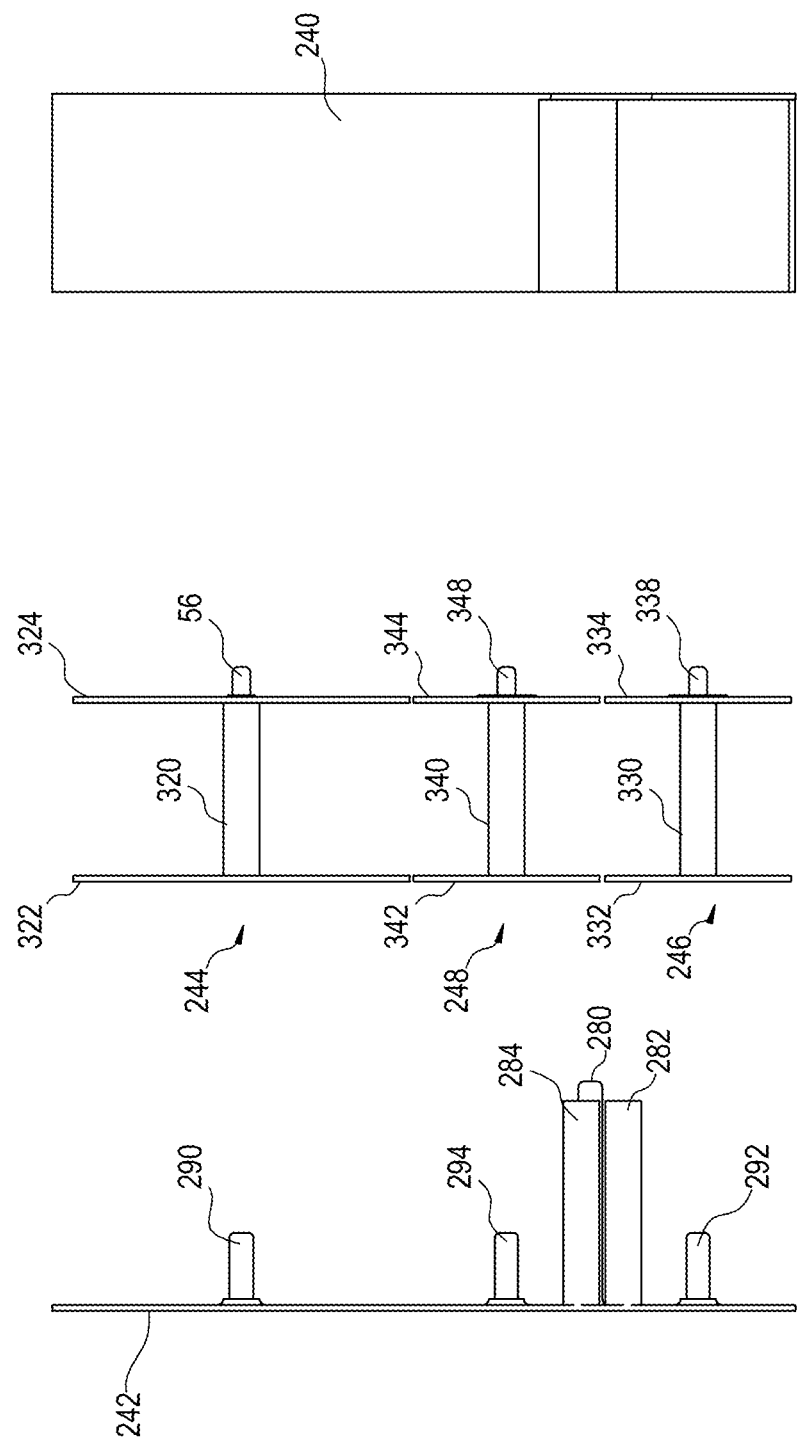
FIG. 9 is front elevation exploded view of the example cartridge assembly.
Figure 10:
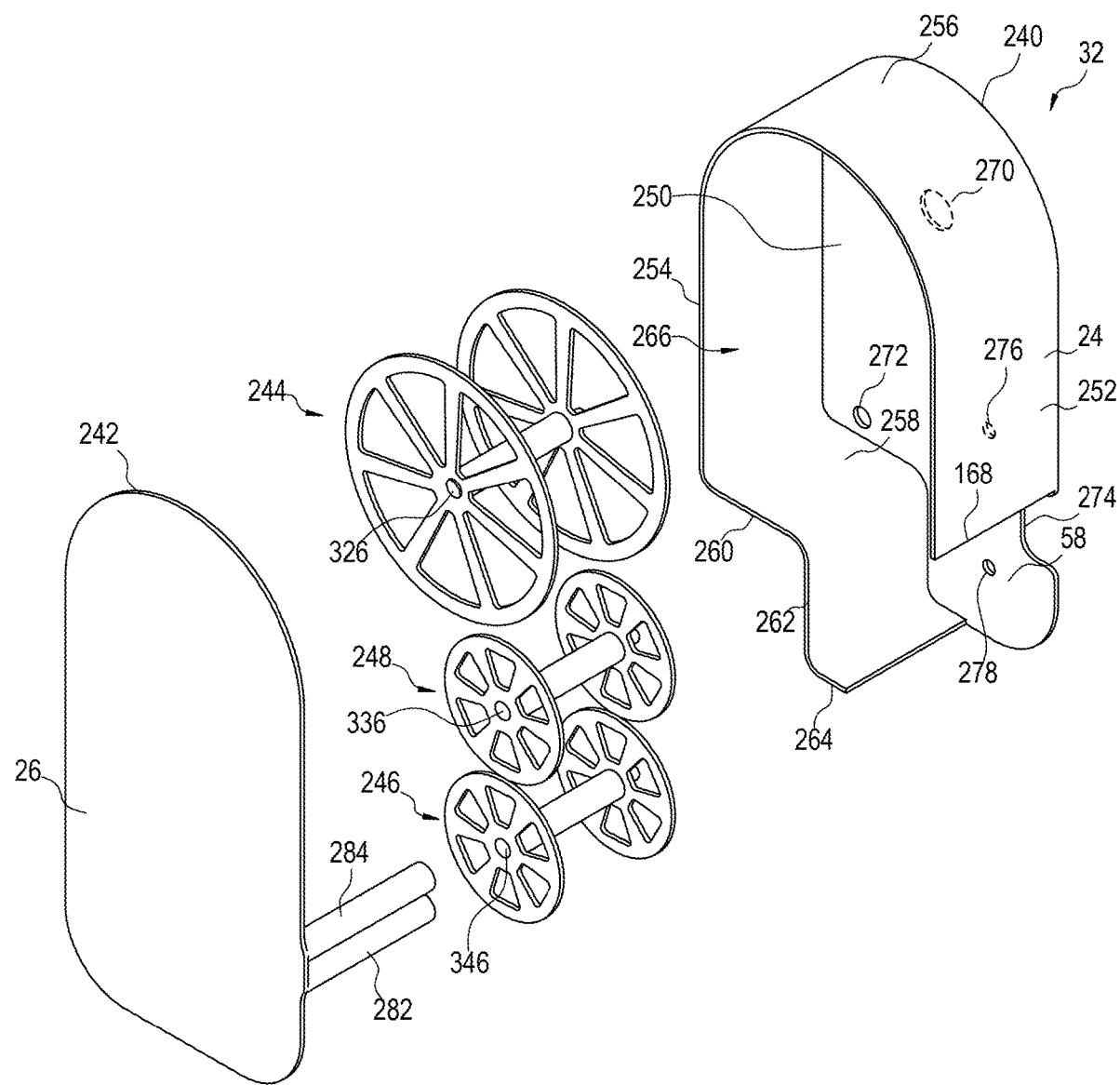
FIG. 10 is a perspective exploded view of the first example cartridge assembly.
Figure 11:
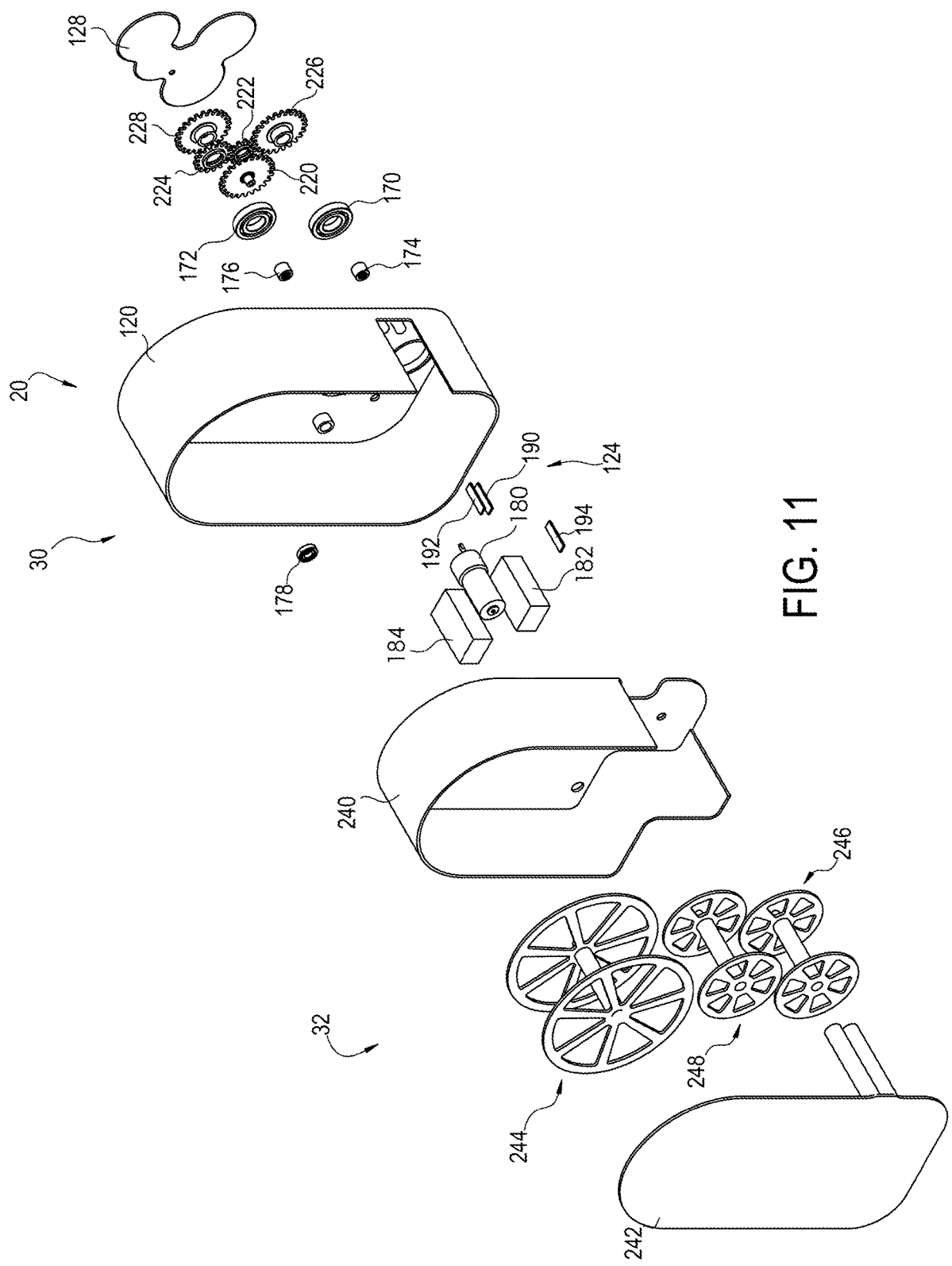
FIG. 11 is an exploded view of the first example dispensing system without a packaging strip of items to be dispensed for clarity.
Figure 12:
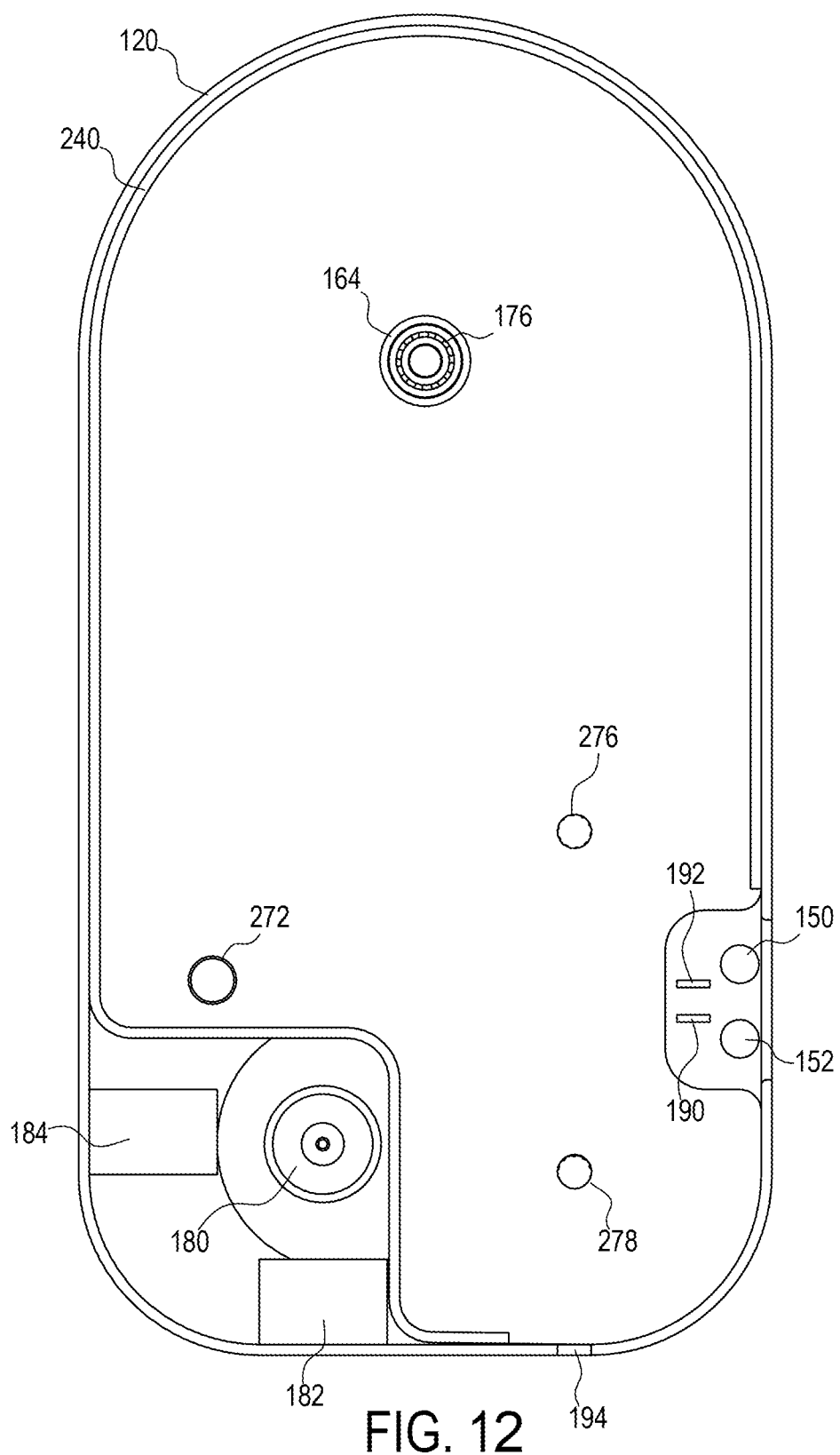
FIG. 12 is a first side elevation view illustrating the first example main housing assembly and the first cartridge housing assembly without a packaging strip of items to be dispensed for clarity.

FIGS. 8-10 illustrate that the example cartridge assembly 32 comprises a cartridge housing 240, a cartridge plate 242, a carrier reel 244, a distal take-up reel 246, and a proximal take-up reel 248. The terms "distal" and "proximal" simply differentiate the take-up reels based on which take-up reel axis is closer to the axis of the carrier reel, but it is possible that the take-up reel axes could be the same distance from the carrier reel axis.

The cartridge housing 240 defines a first cartridge housing wall 250, a second cartridge housing wall 252, a third cartridge housing wall 254, a cartridge top wall 256, and a cartridge inner wall 258. The cartridge inner wall 258 comprises a first portion 260, a second portion 262, and a third portion 264. A cartridge housing main opening 266 is formed by edges of the second cartridge housing wall 252, third cartridge housing wall 254, cartridge top wall 256, and cartridge inner wall 258. A cartridge housing dispensing opening 268 is formed by edges of the second cartridge housing wall 252 and the cartridge inner wall 258. A carrier reel opening 270, a main guide post opening 272, a strip guide post notch 274, and first and second take-up reel openings 274 and 276 are formed in or defined by the first cartridge housing wall 250.

Turning now to the cartridge plate 242, the example cartridge plate 242 is sized and dimensioned to cover the cartridge housing main opening 270. A main guide post 280, first strip guide post 282, and second strip guide post 284 extend from the example cartridge plate 242.

As best shown in FIG. 17, a carrier reel support 290 extends from the first cartridge housing wall 250. FIG. 16 illustrates that first and proximal take-up reel supports 292 and 294 also extend from the first cartridge housing wall 250. FIG. 15 illustrates that first and second strip portion guides 296 and 298 extend from the first cartridge wall 250.

As shown in FIGS. 9 and 17, the carrier reel 244 defines a carrier reel hub 320 and first and second carrier reel flanges 322 and 324. FIG. 17 shows that a carrier reel hub opening 326 extends from the first carrier reel flange 322 into at least a portion of the carrier reel hub 320 and a carrier reel projection 328 extends from the second carrier reel flange 324. The carrier reel hub opening 326 and carrier reel projection 328 are aligned with a carrier reel axis AM defined by the carrier reel hub 320.

As shown in FIGS. 9 and 16, the distal take-up reel 246 defines a distal take-up reel hub 330, a distal take-up reel first flange 332, and a distal take-up reel second flange 334. FIG. 16 shows that a distal take-up reel hub opening 336 extends from the distal take-up reel first flange 332 into at least a portion of the distal take-up reel hub 330 and a distal take-up reel projection 236 extends from the distal take-up reel second flange 334. The distal take-up reel hub opening 336 and distal take-up reel projection 236 are aligned with a distal take-up reel axis A1 defined by the distal take-up reel hub 330.

FIGS. 9 and 16 also illustrate that the proximal take-up reel 248 defines a proximal take-up reel hub 340, a proximal take-up reel first flange 342, and a proximal take-up reel second flange 344. FIG. 16 shows that a proximal take-up reel hub opening 346 extends from the proximal take-up reel first flange 342 into at least a portion of the proximal take-up reel hub 340 and a proximal take-up reel projection 236 extends from the proximal take-up reel second flange 344. The proximal take-up reel hub opening 346 and proximal take-up reel projection 236 are aligned with a proximal take-up reel axis A2 defined by the proximal take-up reel hub 340.

As is apparent from FIGS. 10, 11, 13, and 14, the example carrier reel 244 defines an effective storage capability that is larger than, typically more than twice the effective storage capacity of, the effective storage capacity of each of the first and second take-up reels 246 and 248. In particular, the example carrier reel 244 is sized, dimensioned, and configured to store the entire packaging strip 42 with the items 22 stored thereby. The first and second take-up reels 246 and 248 are sized and dimensioned to store the strip portions 50 and 52, respectively, after the items 22 have been dispensed.

Figure 14:
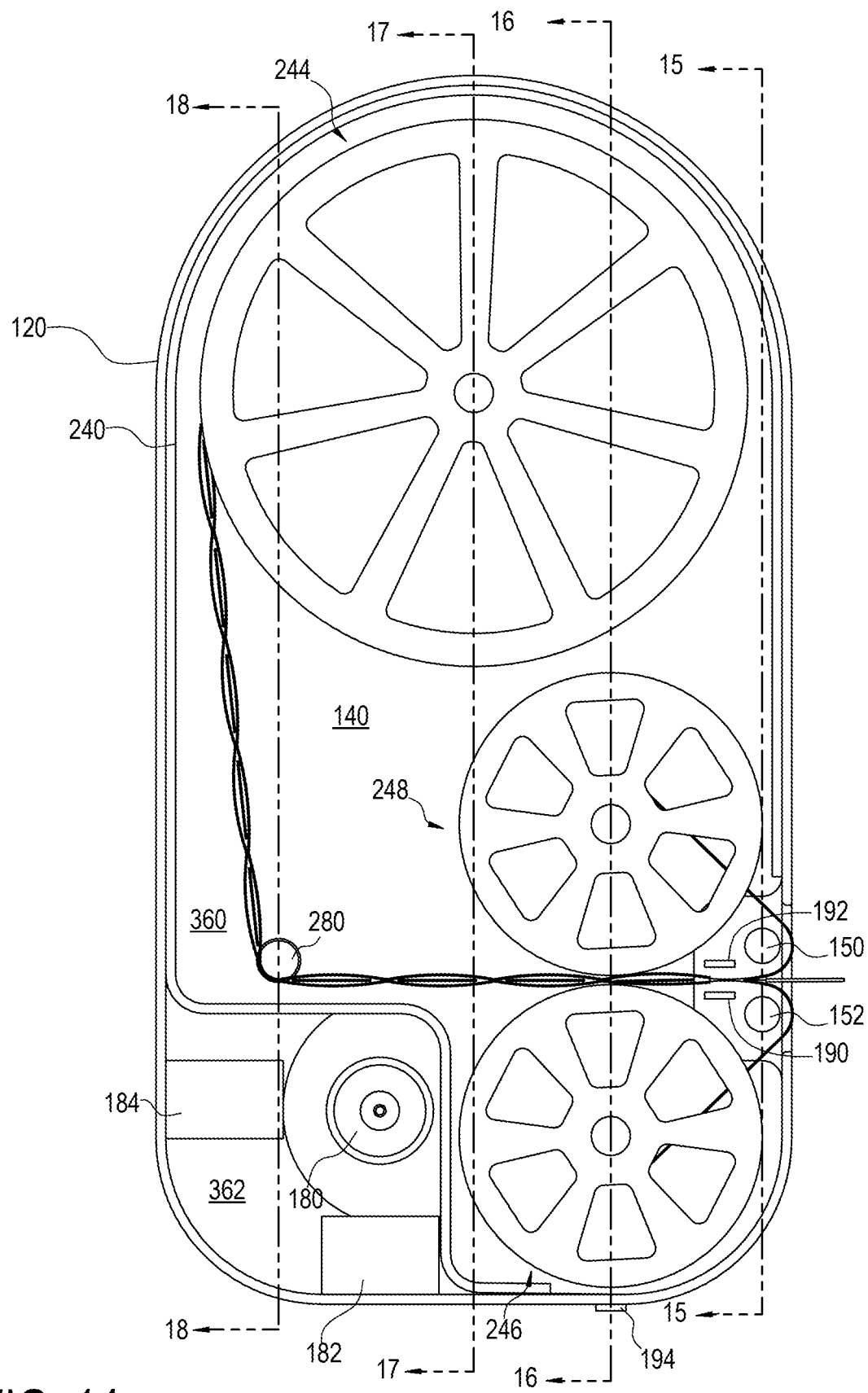
FIG. 14 is a side elevation view illustrating the main housing, cartridge housing, cartridge plate, carrier reel, and first and second take-up reels and also depicting a packaging strip of items being dispensed.

To assemble the first example dispensing system 20, the packaging strip 42 containing the items 22 is wound onto the carrier reel 244. As shown in FIG. 14, the packaging strip 42 is then extended from the carrier reel 244, around the main guide post 280, and between the first and second strip guide posts 282 and 284. As the packaging strip 42 passes between the first and second strip guide posts 282 and 284, the strip portions 50 and 52 are separated from each other and extend to the lower and proximal take-up reels 246 and 248, respectively. In addition, the carrier reel 244 is arranged such that the carrier reel hub opening 326 receives the carrier reel support 290 (FIG. 17). The first and second take-up reels 246 and 248 are arranged such that the distal take-up reel hub opening 336 receives the distal take-up reel support 292 and the proximal take-up reel hub opening 346 receives the proximal take-up reel support 294 (FIG. 16). The outer most ends of the strip portions 50 and 52 of the packaging strip 42 contained on the carrier reel 244 are secured to the first and second take-up reel hubs 330 and 340, respectively.

The cartridge housing 240 is then fixed relative to the cartridge plate 242 to define a cartridge chamber 350, with the carrier reel 244, the first and second take-up reels 246 and 248, and the packaging strip 42 within the cartridge chamber 350. After the cartridge plate 242 is secured to the cartridge housing 240, the carrier reel projection 328 extends through the carrier reel opening 270 (FIG. 17), the first and second take-up reel projections 338 and 348 extend through the first and second take-up reel openings 276 and 278, respectively (FIG. 16), the main guide post 280 extends through the main guide post opening 272, and the first and second strip guide posts 282 and 284 extend through the strip guide post notch 274.

Figure 20:
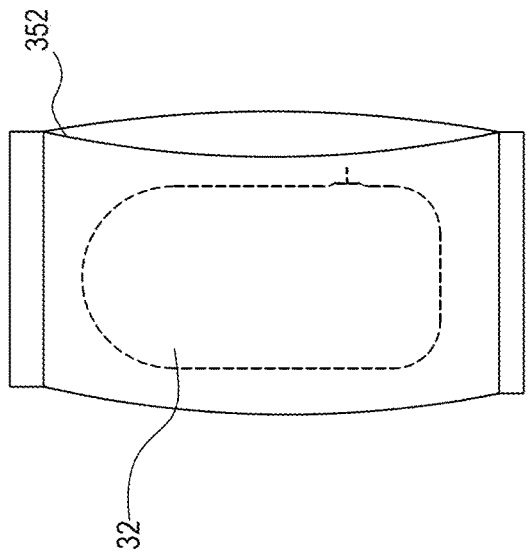
FIG. 20 is a perspective view of a cartridge bag including a cartridge assembly of the present invention.

Once the cartridge assembly 32 has been formed, the cartridge assembly 32 may be packaged and/or sealed by arranging the entire cartridge assembly 32 within a cartridge bag 352 (FIG. 20) and/or arranging seal tape (not shown) over any seams or openings defined by the cartridge assembly 32.

To insert the cartridge assembly 32 into the main housing 120 to dispense the items, the cartridge assembly 32 is removed from the cartridge bag 352 and any seal tape removed from the cartridge assembly 32. The cartridge assembly 32 is then arranged through the main opening 142 of the main housing 120 such that the cartridge housing 240 is within the main chamber 140 of the main housing 120. At this point, the carrier reel projection 328 engages the first ring bearing assembly 170, the distal take-up reel projection 338 engages the first inner bearing assembly 176, the proximal take-up reel projection 348 engages the second inner bearing assembly 178, the main guide post 280 engages the main guide support 152, and the first and second strip guide posts 282 and 284 engage the first and second strip guide supports 152 and 154, respectively. The cartridge assembly 32 is configured to divide the main chamber 140 into first portion 360 and a second portion 362 as perhaps best shown in FIG. 14. The cartridge assembly 32 occupies the first portion 360, while the drive motor 180, power supply 182, and controller 184 are arranged in the second portion 362. A cover, latch, or other mechanism (not shown) may be employed secure the cartridge assembly 32 within the main chamber 140 defined by the main housing 120.

With the cartridge assembly 32 secured within the main chamber 140, the first and second strip guide posts 282 and 284 are arranged adjacent to the dispensing slot 144. To prevent contamination of any of the items 22 stored in the item chambers 40 defined by the packaging strip 42, at least a portion of the first item chamber 40 containing an item 22 is sealed and arranged between the main guide post 280 and the first and second strip guide posts 282 and 284.

Engagement with the external sensor 194 causes the drive motor system 122 to operate such that the drive shaft 186 rotates, causing rotation of the first and second take-up reels 246 and 248 through the first and second inner bearing assemblies 176 and 178 of the transmission system 126. The example transmission system 126 is configured such that the first and second take-up reels 246 and 248 rotate at substantially the same angular velocity.

Rotation of the first and second take-up reels 246 and 248 thus pulls the first and second strip portions 50 and 52 such that the first item chamber 40 is displaced between the first and second strip guide posts 282 and 284. As a leading portion of the first item chamber 40 is displaced between the first and second strip guide posts 282 and 284, the strip portions 50 and 52 defining the first item chamber 40 separate. Continued displacement of the strip portions 50 and 52 cause the item 22 within the first item chamber 40 to protrude through the dispensing slot 144 as illustrated in FIG. 1. The user may grasp the item 22 protruding through the dispensing slot. Engagement with the external sensor 194 repeats the process such that the items 22 within the next and any successive item chambers 40 of the packaging strip 42 are dispensed.

The first example dispensing system allows the next or second item chamber 40 immediately behind the preceding or first item chamber 40 to remain sealed so that the item 22 in the next or second item chamber 40 is not contaminated prior to dispensing. In particular, if the user removing the item 22 from the first or preceding item chamber 40 touches and possibly contaminates the first and second strip portions 50 and 52 defining the first or preceding item chamber 40, any possibly contaminated portions of the first and second strip portions 50 and 52 are rolled up and away on the first and second take-up reels 246 and 248 before the item 22 in the next or second item chamber 40 is dispensed.

Figure 22:
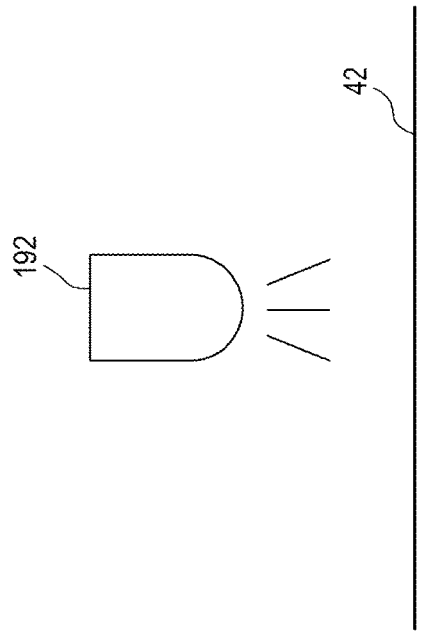
FIG. 22 is a somewhat schematic side elevation view of a first example strip displacement detecting system of the present invention.

As shown in FIGS. 14 and 22, the internal sensor 190, the controller 184, and the external sensor 194 cooperate to ensure that the drive motor 180 rotates the first and second take-up reels 246 and 248 through a desired angular rotation necessary to dispense successive items 22 as described above. Preferably, the internal sensor 190 can sense data (e.g., graphic, QR code, magnetic, textural, shape) carried by the packaging strip 42 to determine linear movement of the packaging strip 42 at or near the first and second strip guide posts 282 and 284.

As shown in FIG. 21, the data carried by the packaging strip 42 may take the form of indicia 370 in form of evenly spaced light portions 372 and dark portion 374 imprinted on the packaging strip 42. In this case, the light source 192 may be used to facilitate detection of the light and dark portion 372 and 374 as shown in FIG. 22. The example light source 192 may be arranged on an opposite side of the packaging strip 42 from the internal sensor 190 as shown in FIG. 14 or on the same side as the internal sensor 190 based on optic needs and space.

Figure 23:
FIG. 23 is a somewhat schematic side elevation view of a second example strip displacement detecting system of the present invention.

FIG. 23 illustrates that the sensor 90 may take the form of a magnetic detector configured to detect passive or active electromagnetic signals from magnetic or other strip (not visible) formed on the packaging strip 42.

Figure 24:
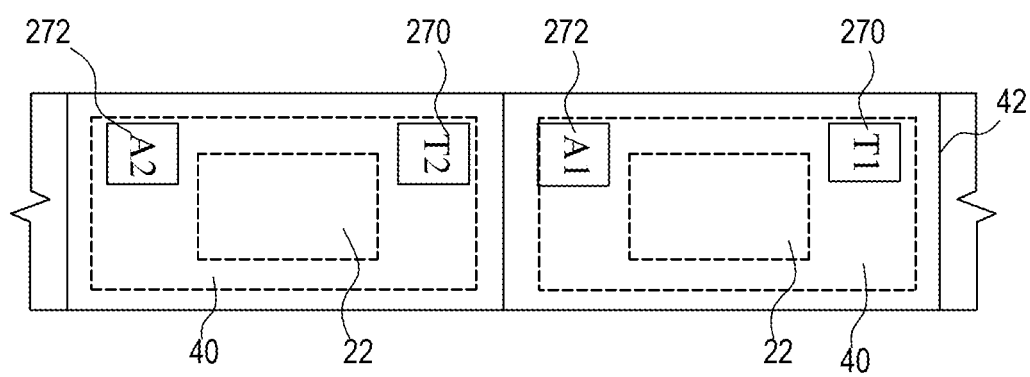
FIG. 24 is a plan view of a section of a second example packaging strip carrying items to be dispensed.

FIG. 24 illustrates the indicia 370 taking the form of characters 376 and 378 indicating the leading and trailing edges of each item chamber 40. These characters 376 and 378 may be read by optical character recognition or other image analysis techniques.

Figure 25:
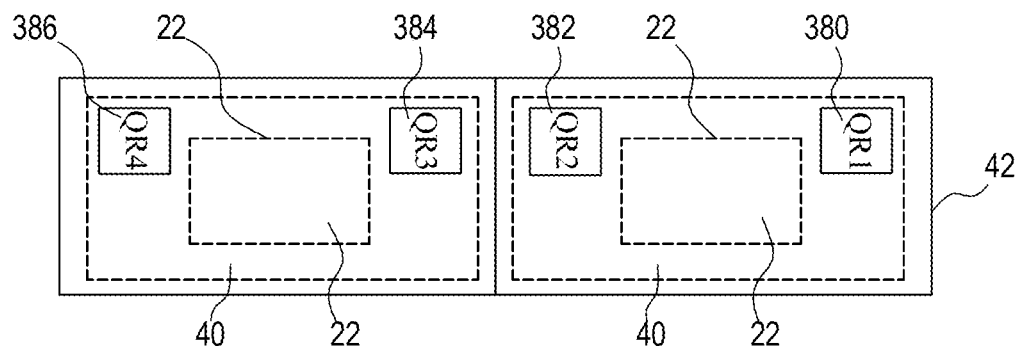
FIG. 25 is a plan view of a section of a third example packaging strip carrying items to be dispensed.

FIG. 25 illustrates the indicia 370 taking the form of QR codes 380-386 indicating the leading and trailing edges and sequential number of each item chamber 40. These characters 380-386 may be read by optical character recognition or other image analysis techniques.

Figure 26:
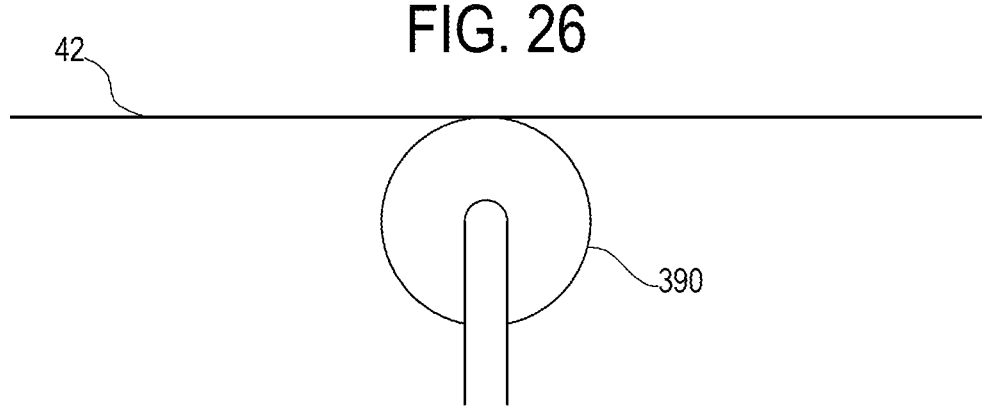
FIG. 26 is a somewhat schematic side elevation view of a roller sensor for measuring linear movement of packaging strip containing items.

FIG. 26 illustrates the use of a roller sensor 390 to sense movement of the packaging strip 42. The roller sensor 390 may be used in addition to or instead of the internal sensor 190 to detect linear movement of the packaging strip 42 to allow the controller 184 to control of the drive motor 180 as described below.

Based on linear movement of the packaging strip 42 and the dimensions of the item chambers 40, the drive motor 180 may be controlled in real time to start and stop as necessary to dispense the items 22 in succession as described above.

Optionally, the controller 184 may operate based on open-loop control (without a sensor such as the internal sensor 190). For example, the drive motor 180 may be stopped and started based on the geometry of the carrier reel 244 and the first and second take-up reels 246 and 248, the length of the packaging strip 42, and the number of items 22 of a particular cartridge assembly 32 previously dispensed at any point in time.

Figure 27:
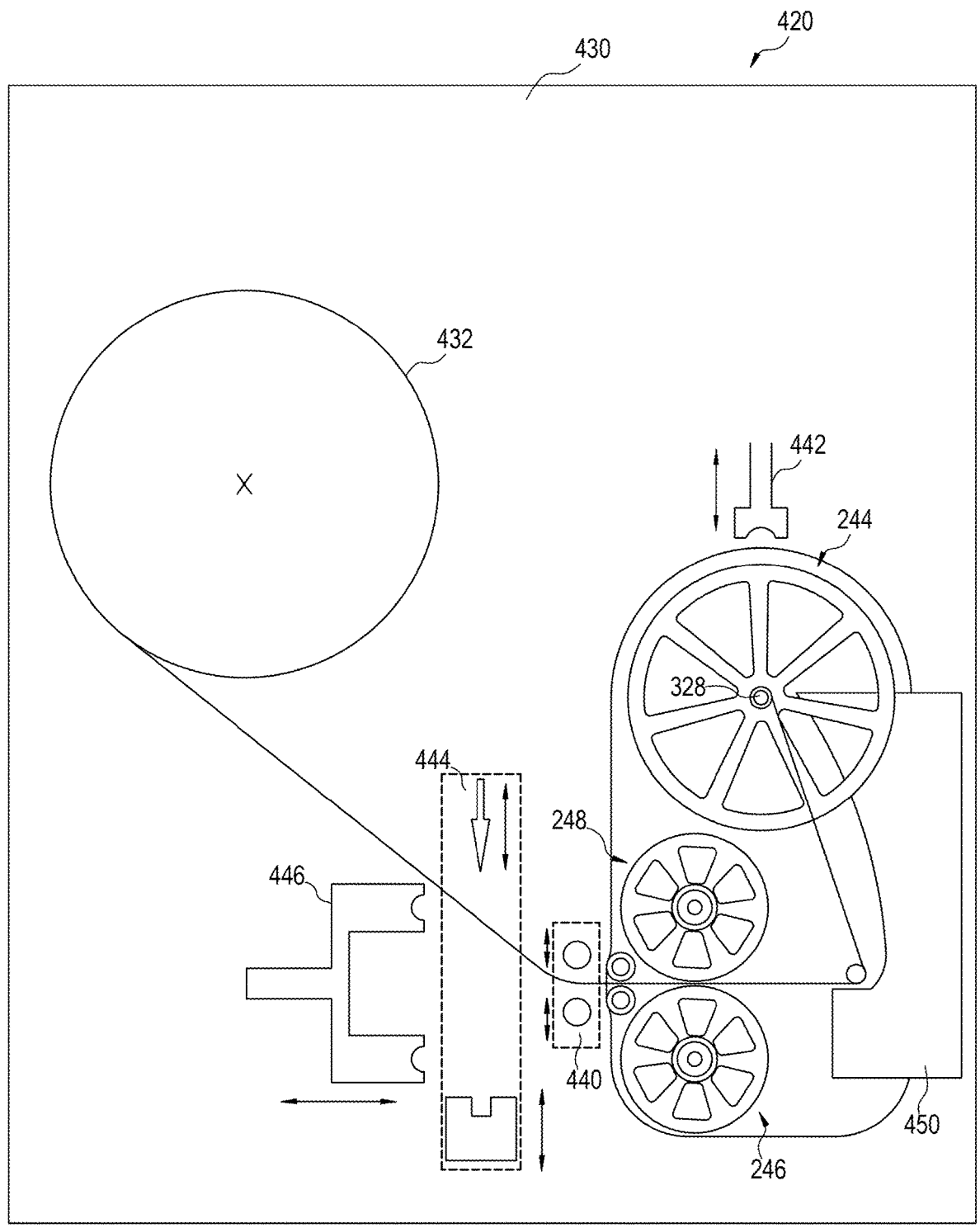
FIG. 27 is a somewhat schematic, front elevation view of a cartridge loading system of the present invention.

Turning now to FIG. 27, depicted therein is an example loading system 420 that may be used to load the cartridge assemblies 32. The example system 420 comprises a fixture 430 and a supply reel 432. The example fixture 430 supports a feed system 440, a carrier reel tamper 442, a cutting system 444, and a take-up reel tamper 446. The supply reel 432 contains a quantity of packaging strip 42 sufficient for multiple carrier reels 244 of the cartridge assemblies 32. The supply reel 432 is supported by the fixture 430, and the fixture 430 further defines a guide surface 450.

In use, a cartridge plate 242 supporting an empty carrier reel 244 and first and second take-up reels 246 and 248 is supported by the fixture 430. The feed system 440 feeds a free end of the packaging strip 42 between the first and second strip guide posts 282 and 284 and the first and second take-up reels 246 and 248. The free end of the packaging strip 42 then is guided up to the carrier reel hub 320 by the guide surface 450. The carrier reel tamper 442 secures the free end of the packaging strip 42 to the carrier reel hub 320. Pressure or heat sensitive adhesive (not visible) may be used to detachably attach the free end of the packaging strip 42 to the carrier reel hub. The carrier reel 244 is then rotated to wind the packaging strip 42 onto the carrier reel 244. When the carrier reel 244 is full, rotation of the carrier reel 244 is stopped. A sensor 260 may be supported by the fixture 430 to determine when the carrier reel 244 is completely loaded.

The cutting system 444 then cuts the packaging strip 42. The take-up reel tamper 446 then secures the free ends of the strip portions 50 and 52 of the packaging strip 42 to the take-up reel hubs 330 and 340, respectively. Pressure or heat sensitive adhesive (not visible) may be used to detachably attach the free ends of the strip portions 50 and 52 of the packaging strip 42 to the take-up reel hubs 330 and 340, respectively. The example feed system 440 is displaced at least temporarily during movement of the take-up reel tamper 446.

The cartridge plate 242 supporting a carrier reel 244 and first and second take-up reels 246 and 248 is removed from the fixture 430, and another cartridge plate 242 supporting an empty carrier reel 244 and first and second take-up reels 246 and 248 is supported by the fixture 430. The process is then repeated to load the next carrier reel 244.

To minimize waste of product 22, the packaging strip 42 stored on the carrier reel may have a predetermined number of full item chambers 40 separated by blank sections with empty item chambers 42 or a different adhesive region pattern to facilitate cutting and feeding of the free end (after the cut) into the empty cartridge sub-assembly and the securing of the first and second strip portions 50 and 52 to the first and second take-up reels 246 and 248, respectively.

Figure 28:
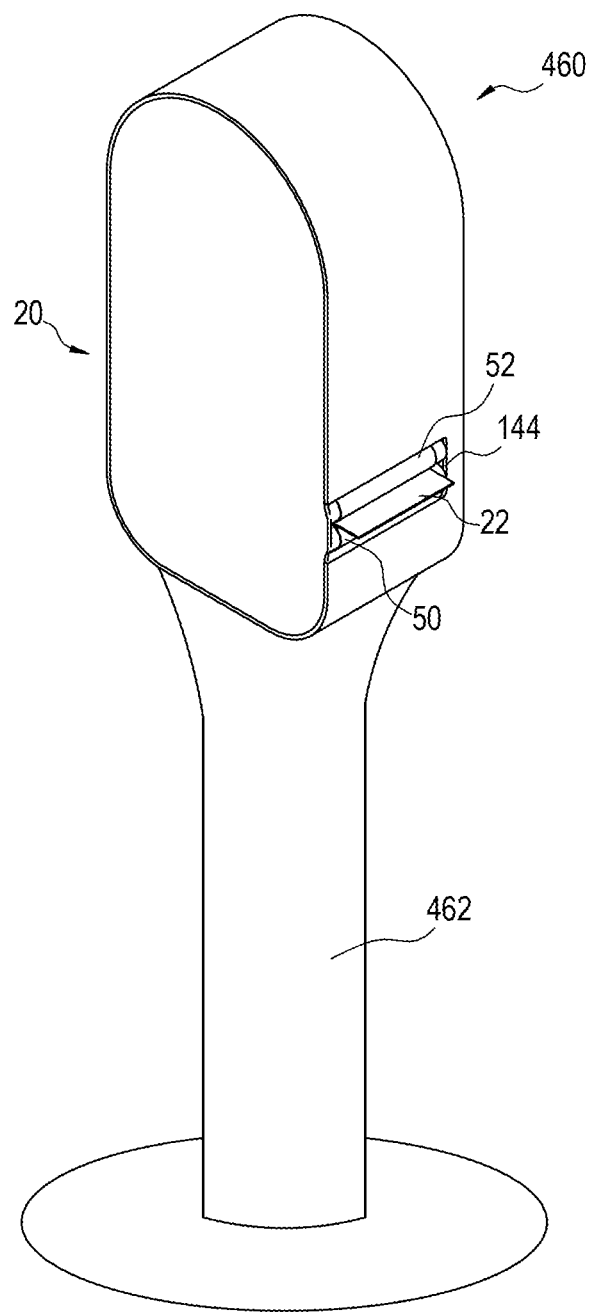
FIG. 28 is a perspective view of a second example dispensing system of the present invention.

Turning now to FIG. 28 of the drawing, depicted therein is a second example dispensing system 460 of the present invention. The second example dispensing system 460 comprises a podium 462 in addition to the first example dispensing system 20. While the first example dispensing system 20 is preferably (but not necessarily) supported on a vertical surface such as a wall or cabinet, the second example dispensing system 460 is preferably (but not necessarily) supported on a horizontal surface such as a floor or the ground.

What is claimed is:

1. A dispensing system for items comprising:
    a main housing assembly defining a dispensing opening and comprising
        a drive system, and
        a main housing supporting a main guide support and first and second strip guide supports; and
    a cartridge assembly comprising
        a carrier reel,
        distal and proximal take-up reels,
        a main guide post adapted to engage the main guide support;
        a first strip guide post adapted to engage the first strip guide support,
        a second strip guide post adapted to engage the second strip guide support, and
        a packaging strip comprising first and second strip portions detachably secured to define a plurality of item chambers, where at least one item is enclosed within each of the item chambers; wherein
    the carrier reel is adapted to store the packaging strip;
    the distal take-up reel is operatively connected to the first strip portion;
    the proximal take-up reel is operatively connected to the second strip portion;
    the drive system is operatively connected to the proximal and distal take-up reels; and
    operation of the drive system rotates the distal and proximal take-up reels such that
        the packaging strip is unwound from the main wheel,
        the first strip portion is wound onto the distal take-up reel,
        the second strip portion is wound onto the proximal take-up reel, and
        the items are dispensed through the dispensing opening.

2. A dispensing system as recited in claim 1, in which:
    the main housing assembly comprises a main housing supporting first, second, and third bearing assemblies;
    the carrier wheel defines a carrier wheel projection adapted to engage the first bearing assembly;
    the distal take-up reel defines a distal take-up reel projection adapted to engage the second bearing assembly; and
    the proximal take-up reel defines a proximal take-up reel projection adapted to engage the third bearing assembly.

3. A dispensing system as recited in claim 1, in which the cartridge assembly comprises:
    a cartridge housing; and
    a cartridge plate adapted to support the carrier reel and the distal and proximal take-up reels such that
        a carrier reel projection of the carrier reel extends through a carrier reel opening in the cartridge housing,
        a distal take-up reel projection of the distal take-up reel extends through a first take-up reel opening in the cartridge housing, and
        a proximal take-up reel projection of the proximal take-up reel extends through a second take-up reel opening in the cartridge housing.

4. A dispensing system as recited in claim 1, in which drive system comprises:
    a drive motor defining a drive shaft; and
    a transmission system operatively connected between the drive shaft and the distal and proximal take-up reels such that operation of the drive motor causes rotation of the distal and proximal take-up reels.

5. A dispensing system as recited in claim 4, in which the drive system further comprises:
    a controller operatively connected to the drive motor; and
    an interior sensor arranged to generate a control signal associated with movement of the packaging strip; whereby
    the controller controls operation of the drive motor based on the control signal generated by the interior sensor.

6. A dispensing system as recited in claim 4, in which the transmission system comprises a plurality of gears arranged between the drive shaft and the distal and proximal take-up reels.

7. A dispensing system as recited in claim 4, in which the transmission system comprises:
- a primary drive gear operatively connected to the drive shaft;
- a secondary drive gear arranged to engage the primary drive gear;
- a tertiary drive gear arranged to engage the primary drive gear;
- a first take-up gear arranged to engage the primary drive gear; and
- a second take-up gear arranged to engage the tertiary drive gear; whereby
- rotation of the first take-up gear causes rotation of the distal take-up reel; and
- rotation of the second take-up gear causes rotation of the proximal take-up reel.

8. A dispensing system as recited in claim 5, in which the drive system further comprises an exterior sensor arranged to generate a dispense authorization signal based on action by a user of the dispensing system, where the controller further controls operation of the drive motor based on the dispense authorization signal generated by the exterior sensor.

9. A method of dispensing items comprising the steps of:
- providing first and second packaging strip portions;
- forming a packaging strip by adhering the first packaging strip portion to the second packaging strip portion such that each of the items is sealed within an item chamber;
- arranging at least a portion of the packaging strip on a carrier reel;
- securing a first packaging strip portion end of the first packaging strip portion to a distal take-up reel;
- securing a second packaging strip portion end of the second packaging strip portion to a proximal take-up reel;
- supporting the carrier reel, the packaging strip, and the distal and proximal take-up reels on a cartridge plate;
- forming a cartridge assembly by engaging the cartridge plate with a cartridge housing;
- providing a main housing defining a dispensing opening;
- supporting a drive system on the main housing;
- arranging the cartridge assembly within the main housing such that the drive system engages the distal and proximal take-up reels; and
- dispensing items through the dispensing opening by operating the drive system to rotate the distal and proximal take-up reels such that
  - the packaging strip is unwound from the main wheel,
  - the first strip portion is wound onto the distal take-up reel,
  - the second strip portion is wound onto the proximal take-up reel; wherein
- the step of supporting the drive system on the main housing comprises the steps of
  - operatively connecting a controller to a drive motor defining a drive shaft, and
  - operatively connecting a transmission system between the drive shaft and the distal and proximal take-up reels such that operation of the drive motor causes rotation of the distal and proximal take-up reels; and
- the step of operatively connecting the transmission system between the drive shaft and the distal and proximal take-up reels comprises the steps of operatively connecting a primary drive gear operatively connected to the drive shaft,
  - arranging a secondary drive gear to engage the primary drive gear,
  - arranging a tertiary drive gear to engage the primary drive gear,
  - arranging a first take-up gear to engage the primary drive gear,
  - arranging a second take-up gear to engage the tertiary drive gear,
  - arranging the first take-up gear such that rotation of the first take-up gear causes rotation of the distal take-up reel, and
  - arranging the second take-up gear such that rotation of the second take-up gear causes rotation of the proximal take-up reel.

10. A method as recited in claim 9, in which the step of providing the main housing assembly comprises the step of forming first, second, and third bearing assemblies on a main housing, the method further comprising the steps of:
- supporting a carrier wheel projection defined by the carrier wheel with the first bearing assembly;
- supporting a distal take-up wheel projection defined by the distal take-up wheel with the second bearing assembly; and
- supporting a proximal take-up wheel projection defined by the proximal take-up wheel with the third bearing assembly.

11. A method as recited in claim 10, in which the step of supporting the drive system on the main housing further comprises the steps of:
- arranging an interior sensor to generate a control signal associated with movement of the packaging strip; and
- controlling operation of the drive motor based on the control signal generated by the interior sensor.

12. A method as recited in claim 11, in which the step of supporting the drive system on the main housing further comprises the steps of:
- arranging an exterior sensor to generate a dispense authorization signal based on action by a user of the dispensing system; and
- controlling operation of the drive motor based on the dispense authorization signal generated by the exterior sensor.

13. A dispensing system for items comprising:
- a main housing assembly defining a dispensing opening and comprising
  - a drive system,
  - a main housing supporting a main guide support and first and second strip guide supports, and
  - first, second, and third bearing assemblies supported by the main housing; and
- a cartridge assembly comprising
  - a cartridge plate,
  - a cartridge housing that engages the cartridge plate to define a cartridge chamber,
  - a carrier reel supported by the cartridge plate within the cartridge chamber, the carrier wheel defining a carrier wheel projection adapted to engage the first bearing assembly, and
  - distal and proximal take-up reels supported by the cartridge plate within
    - the cartridge chamber, where
    - the distal take-up reel defines a distal take-up reel projection adapted to engage the second bearing assembly, and the proximal take-up reel defines a proximal take-up reel projection adapted to engage the third bearing assembly a main guide post adapted to engage the main guide support;

a first strip guide post adapted to engage the first strip guide support; and a second strip guide post adapted to engage the second strip guide support, and a packaging strip comprising first and second strip portions detachably secured to define a plurality of item chambers, where at least one item is enclosed within each of the item chambers; wherein the carrier reel is adapted to store the packaging strip;

the distal take-up reel is operatively connected to the first strip portion;

the proximal take-up reel is operatively connected to the second strip portion; and the drive system is operatively connected to the proximal and distal take-up reels such that operation of the drive system rotates the distal and proximal take-up reels such that the packaging strip is unwound from the main wheel, the first strip portion is wound onto the distal take-up reel, the second strip portion is wound onto the proximal take-up reel, and the items are dispensed through the dispensing opening.

14. A dispensing system as recited in claim claim 13, in which:

a carrier reel projection of the carrier reel extends through a carrier reel opening in the cartridge housing, a distal take-up reel projection of the distal take-up reel extends through a first take-up reel opening in the cartridge housing, and a proximal take-up reel projection of the proximal take-up reel extends through a second take-up reel opening in the cartridge housing.

15. A dispensing system as recited in claim 13, in which drive system comprises:

a drive motor defining a drive shaft;

a transmission system operatively connected between the drive shaft and the distal and proximal take-up reels such that operation of the drive motor causes rotation of the distal and proximal take-up reels;

a controller operatively connected to the drive motor;

an interior sensor arranged to generate a control signal associated with movement of the packaging strip; and an exterior sensor arranged to generate a dispense authorization signal based on action by a user of the dispensing system; whereby the controller controls operation of the drive motor based on the control signal generated by the interior sensor and based on the dispense authorization signal generated by the exterior sensor.

16. A dispensing system for items comprising:

a main housing assembly defining a dispensing opening and comprising a drive system;

a cartridge assembly comprising a carrier reel, distal and proximal take-up reels, and a packaging strip comprising first and second strip portions detachably secured to define a plurality of item chambers, where at least one item is enclosed within each of the item chambers;

a drive motor defining a drive shaft; and a transmission system operatively connected between the drive shaft and the distal and proximal take-up reels such that operation of the drive motor causes rotation of the distal and proximal take-up reels, the transmission system comprising a primary drive gear operatively connected to the drive shaft, a secondary drive gear arranged to engage the primary drive gear, a tertiary drive gear arranged to engage the primary drive gear, a first take-up gear arranged to engage the primary drive gear, and a second take-up gear arranged to engage the tertiary drive gear;

whereby rotation of the first take-up gear causes rotation of the distal take-up reel; and rotation of the second take-up gear causes rotation of the proximal take-up reel;

wherein the carrier reel is adapted to store the packaging strip;

the distal take-up reel is operatively connected to the first strip portion;

the proximal take-up reel is operatively connected to the second strip portion;

the drive system is operatively connected to the proximal and distal take-up reels; and operation of the drive system rotates the distal and proximal take-up reels such that the packaging strip is unwound from the main wheel, the first strip portion is wound onto the distal take-up reel, the second strip portion is wound onto the proximal take-up reel, and the items are dispensed through the dispensing opening.

* * * * *